United States Patent
Malewicz et al.

(10) Patent No.: US 9,504,569 B2
(45) Date of Patent: Nov. 29, 2016

(54) TRANSAPICAL DELIVERY DEVICE AND METHOD OF USE

(75) Inventors: Andrzej M. Malewicz, Minneapolis, MN (US); Matthew W. Weston, Little Canada, MN (US); David Elizondo, Champlin, MN (US); Daniel C. Weber, Plymouth, MN (US)

(73) Assignee: Medtronic 3F Therapeutics, Inc., Irvine, CA (US)

( * ) Notice: Subject to any disclaimer, the term of this patent is extended or adjusted under 35 U.S.C. 154(b) by 99 days.

(21) Appl. No.: 12/870,614

(22) Filed: Aug. 27, 2010

(65) Prior Publication Data

US 2011/0106246 A1    May 5, 2011

Related U.S. Application Data

(60) Provisional application No. 61/238,063, filed on Aug. 28, 2009, provisional application No. 61/287,030, filed on Dec. 16, 2009, provisional application No. 61/322,501, filed on Apr. 9, 2010.

(51) Int. Cl.
*A61F 2/24* (2006.01)
*A61F 2/95* (2013.01)

(52) U.S. Cl.
CPC .......... *A61F 2/2439* (2013.01); *A61F 2/2436* (2013.01); *A61F 2/2412* (2013.01); *A61F 2002/9517* (2013.01); *A61F 2002/9522* (2013.01)

(58) Field of Classification Search
CPC .......... A61F 2/95; A61F 2/962; A61F 2/966; A61F 2/2427; A61F 2/2436; A61F 2002/95; A61F 2002/9665; A61F 2/2466

USPC ........................................................ 623/2.11
See application file for complete search history.

(56) References Cited

U.S. PATENT DOCUMENTS

| | | | |
|---|---|---|---|
| 5,626,604 A | 5/1997 | Cottone, Jr. | |
| 5,738,674 A | 4/1998 | Williams et al. | |
| 5,911,752 A | 6/1999 | Dustrude et al. | |
| 6,082,990 A | 7/2000 | Jackson et al. | |
| 6,141,855 A | 11/2000 | Morales | |
| 6,167,605 B1 | 1/2001 | Morales | |
| 6,240,615 B1 | 6/2001 | Kimes et al. | |
| 6,776,791 B1 * | 8/2004 | Stallings | A61F 2/07 623/1.11 |
| 7,290,322 B2 | 11/2007 | Cai et al. | |

(Continued)

FOREIGN PATENT DOCUMENTS

| | | |
|---|---|---|
| CA | 2572737 | 7/2007 |
| CN | 101460115 | 6/2009 |

OTHER PUBLICATIONS http://www.merriam-webster.com/dictionary/terminal, Merriam-Webster, Terminal, as accessed on Oct. 23, 2015.*

(Continued)

*Primary Examiner* — Todd J Scherbel

(57) ABSTRACT

A delivery device for a stented heart valve that includes a handle, an inner catheter shaft extending from the handle and having an enlarged bumper element at a distal end, an outer catheter shaft extending from the handle and slidably coupled around the inner catheter shaft, and a retraction mechanism for controlling longitudinal movement of the outer catheter shaft relative to the inner catheter shaft. The outer catheter shaft includes a generally cylindrical housing at a distal end that is structured to receive the bumper element therein.

16 Claims, 28 Drawing Sheets

(56) References Cited

U.S. PATENT DOCUMENTS

| | | |
|---|---|---|
| 7,530,253 B2 | 5/2009 | Spenser et al. |
| 7,895,876 B2 | 3/2011 | Spenser et al. |
| 2002/0138966 A1 | 10/2002 | Motsenbocker |
| 2003/0065381 A1 | 4/2003 | Solar et al. |
| 2004/0267348 A1* | 12/2004 | Gunderson et al. ......... 623/1.12 |
| 2005/0027305 A1 | 2/2005 | Shiu et al. |
| 2005/0143752 A1 | 6/2005 | Schwager et al. |
| 2006/0229697 A1* | 10/2006 | Gerdts et al. ............... 623/1.11 |
| 2009/0054976 A1 | 2/2009 | Tuval et al. |
| 2009/0138079 A1* | 5/2009 | Tuval et al. ................ 623/2.11 |
| 2010/0217382 A1* | 8/2010 | Chau et al. ................. 623/1.26 |
| 2010/0292784 A1* | 11/2010 | Giannetti et al. ........... 623/2.11 |

OTHER PUBLICATIONS

State Intellectual Property Office of P.R.C. Search Report, Jan. 30, 2014.

\* cited by examiner

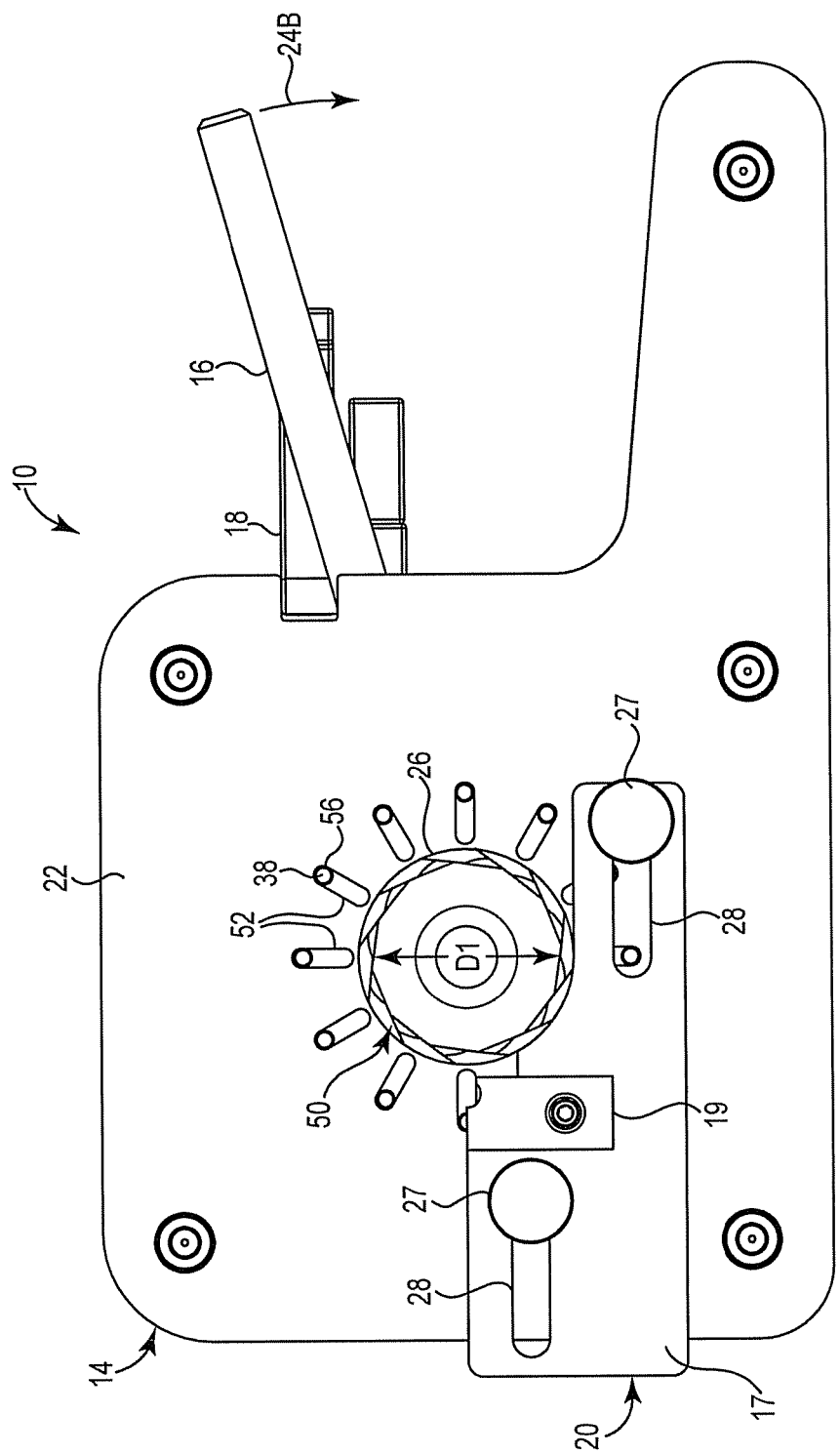

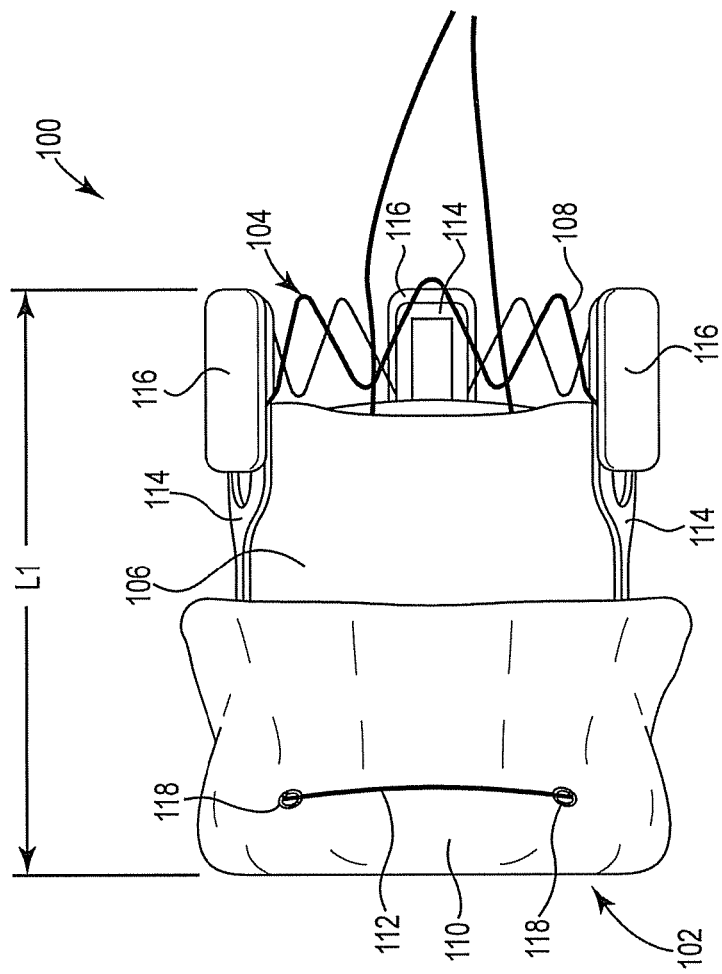
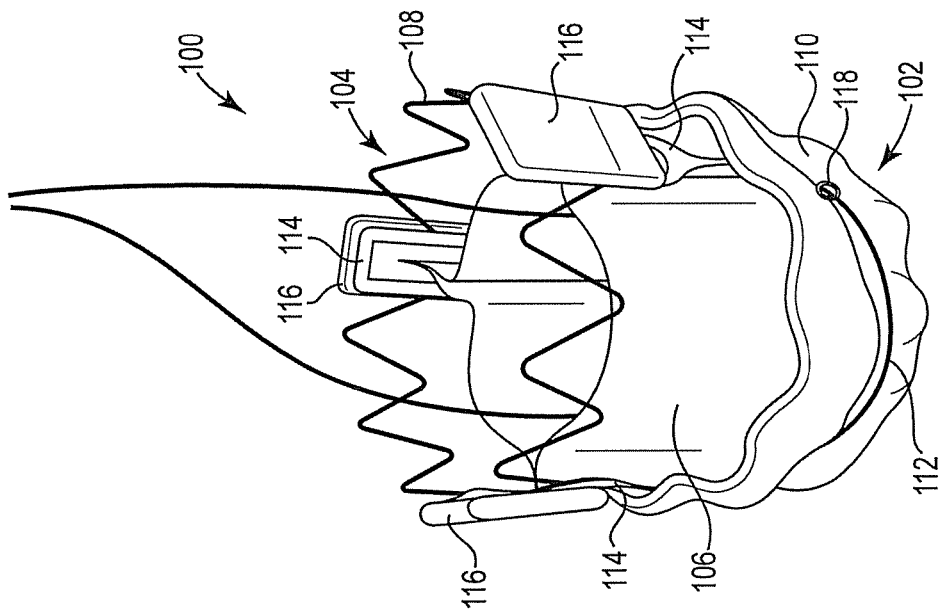
Fig. 12A
Fig. 12B

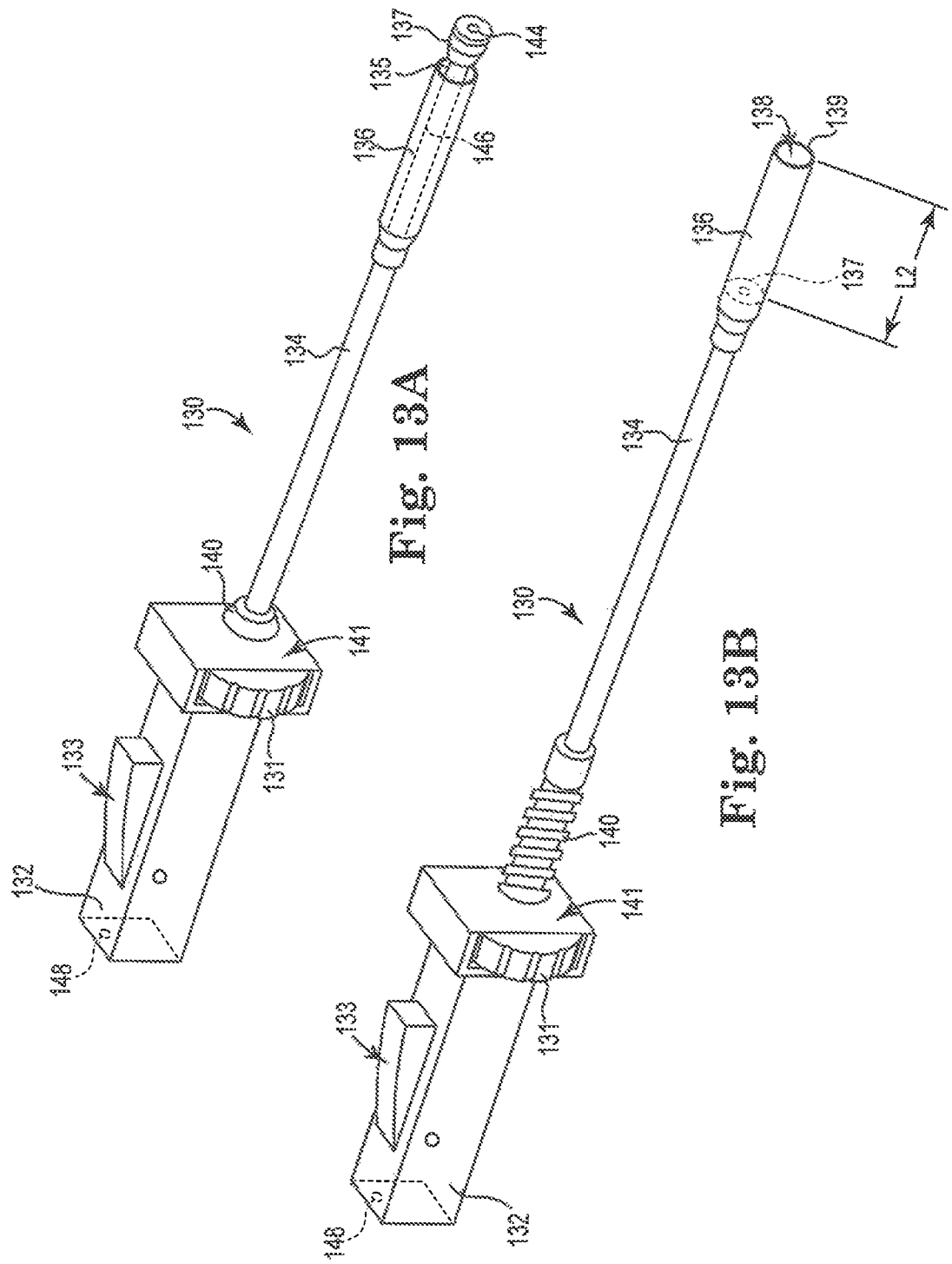

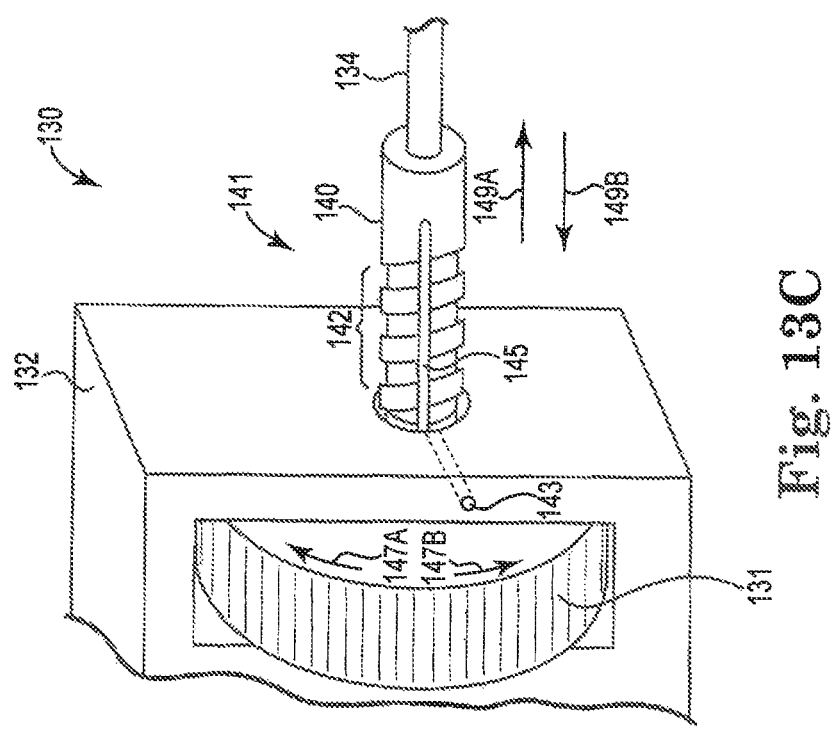

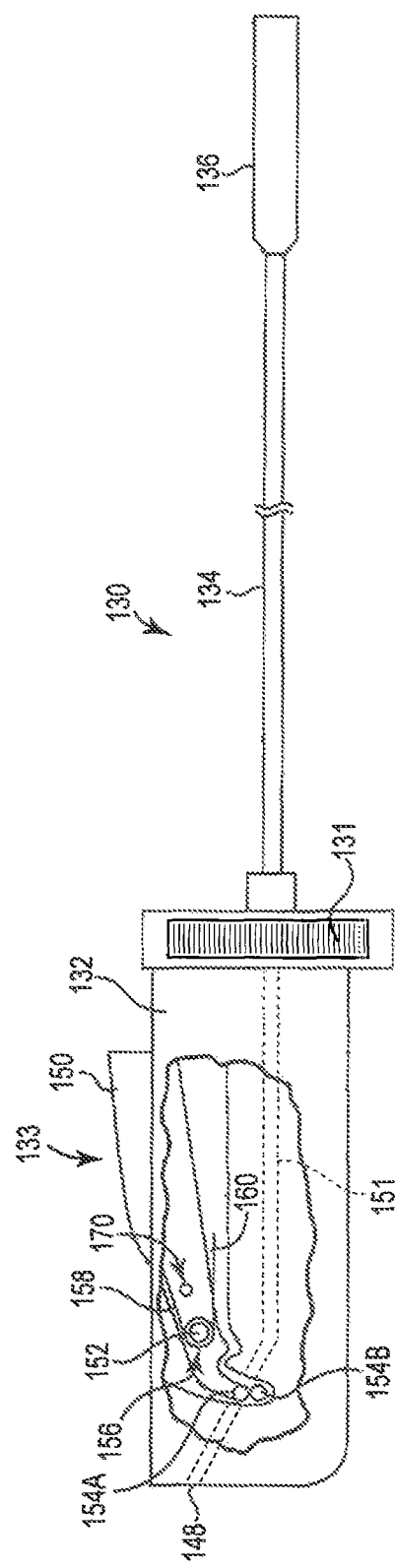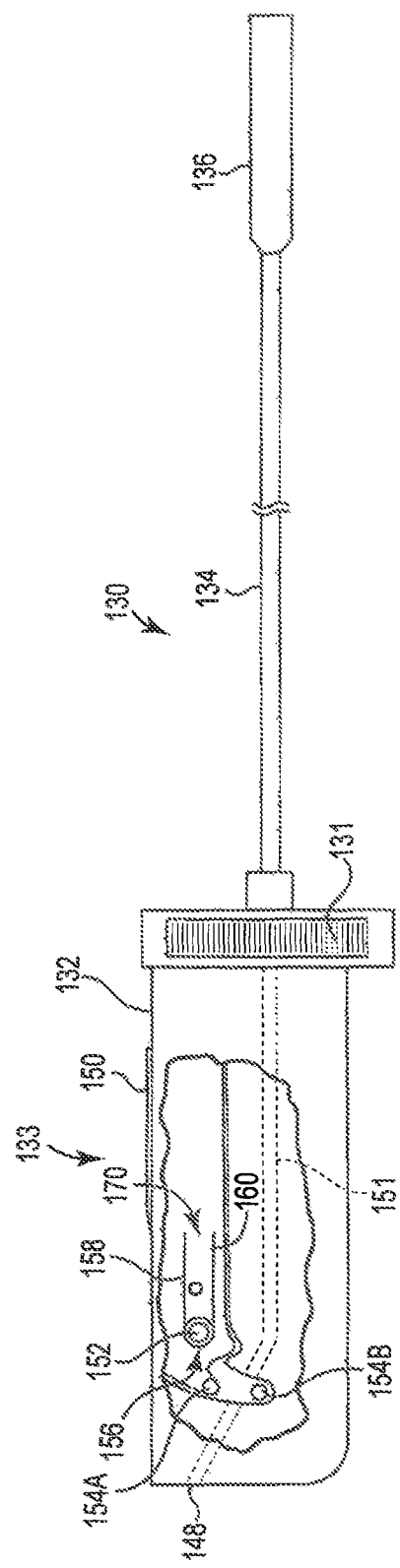

TRANSAPICAL DELIVERY DEVICE AND METHOD OF USE

CROSS-REFERENCE TO RELATED APPLICATIONS

This application claims priority under 35 U.S.C. §119(e)(1) to U.S. Provisional Patent Application Ser. Nos. 61/238,063, filed Aug. 28, 2009; 61/287,030, filed Dec. 16, 2009; and 61/322,501, filed Apr. 9, 2010; the entire teachings of each of which are incorporated herein by reference.

FIELD

The present disclosure is generally directed to a heart valve delivery device and method of use. More particularly, the present disclosure is directed to a transapical delivery device for delivering a heart valve to an implantation site.

BACKGROUND

Heart valve replacement is required when a patient's heart valve becomes diseased or damaged. Surgically implanted heart valve prostheses have extended the life expectancy of many patients with defective heart valves. Such prostheses can be either mechanical or biological (tissue valves), stented or stentless, and may be implanted into an aortic, mitral, tricuspid, or pulmonary position.

Stented heart valves made from flexible material or from materials that exhibit shape memory characteristics promise less complicated and faster valve implantation procedures. The stents supporting the heart valves are generally cylindrical in shape and are structured to be crimped so as to reduce their size for delivery to a target site. The stents may be either self-expanding or non self-expanding. Self-expanding stents may be formed from any suitable shape memory material, such as Nitinol. Non self-expanding stents are typically expanded via an inflation means or mechanical expansion means. Stented heart valves are sometimes referred to as suture-less valves because they may be implanted and secured into the annulus without the use of sutures.

As appreciated by those of ordinary skill in the art, it is desirable to crimp or otherwise radially compress the stent in a substantially uniform manner to minimize the variation in pressures applied to the stent. Such pressure variations may lead to deformation of the stent, which may reduce the ability of the stent to securely maintain the heart valve at the target location. Thus, if a stent is crimped in a non-uniform manner, it is typically either re-crimped or thrown away. Re-crimping of stents is not desirable because the repeated application of force on the stent may cause fatigue or weakening of the stent structure. Disposing of poorly crimped stents is also not desirable due to the increased costs associated with the waste. This is especially true with stented heart valves because the stent and the heart valve are attached together and must be disposed of as a single unit.

A number of different strategies have been used to repair or replace a defective heart valve with stented replacement valves. Surgical valve repair or replacement surgery involves a gross thoracotomy, usually in the form of a median sternotomy. In this procedure, a saw or other cutting instrument is used to cut the sternum longitudinally and the two opposing halves of the anterior or ventral portion of the rib cage are spread apart. A large opening into the thoracic cavity is thus created, through which the surgeon may directly visualize and operate upon the heart and other thoracic contents. The patient must be placed on cardiopulmonary bypass for the duration of the surgery. Open-chest valve replacement surgery has the benefit of permitting the direct implantation of the replacement valve at its intended target site. For example, the stented replacement valve may be delivered to the target site with a delivery catheter or the like. Once positioned in the desired location, the stent may be re-expanded to secure the replacement heart valve in place by exerting radial forces against the internal walls of the implantation annulus.

Minimally invasive percutaneous valve replacement procedures have emerged as an alternative to open-chest surgery. Unlike open-heart procedures, percutaneous procedures are indirect and involve intravascular catheterization from a vessel, such as femoral, subclavian and the like, to the heart. Because the minimally invasive approach requires only a small incision, it allows for a faster recovery for the patient with less pain and the promise of less bodily trauma. This, in turn, reduces the medical costs and the overall disruption to the life of the patient.

The use of a minimally invasive approach, however, introduces new complexities to surgery. An inherent difficulty in the minimally invasive percutaneous approach is the limited space that is available within the vasculature. Unlike open-heart surgery, minimally invasive heart surgery offers a surgical field that is only as large as the diameter of a blood vessel. Consequently, the introduction of tools and prosthetic devices becomes a great deal more complicated. The device must be dimensioned and configured to permit the device to be introduced into the vasculature, maneuvered therethrough, and positioned at a desired implant location.

In addition to surgical and minimally invasive percutaneous procedures, it is also possible to implant a replacement valve through the apical area of the heart. The apical area of the heart is generally the blunt rounded inferior extremity of the heart formed by the left and right ventricles. In normal healthy humans, the apical area generally lies behind the fifth left intercostal space from the mid-sternal line. The unique anatomical structure of the apical area permits the introduction of various surgical devices and tools into the heart without significant disruption of the natural mechanical and electrical heart function. Because transapical procedures allow direct access to the heart and great vessels through the apex, they are not limited by the size constraints which are presented by percutaneous surgical methods. While access to the heart through the femoral vessels in percutaneous methods are limited to the diameter of the vessel (approximately 8 mm), access to the heart through the apical area is significantly larger (approximately 25 mm). Thus, apical access to the heart permits greater flexibility with respect to the types of devices and surgical methods that may be performed in the heart and great vessels.

Thus, because the transapical approach is different than conventional open-chest and minimally invasive percutaneous approaches, a new system and method for deploying a heart valve using transapical techniques are needed.

SUMMARY

The present disclosure addresses the foregoing needs by providing a novel delivery device for a stented heart valve including a handle, an inner catheter shaft extending from the handle and having an enlarged bumper element at a distal end, an outer catheter shaft extending from the handle and slidably coupled around the inner catheter shaft, and a retraction mechanism for controlling longitudinal movement of the outer catheter shaft relative to the inner catheter shaft. The outer catheter shaft includes a generally cylindrical housing at a distal end that is structured to receive the bumper element therein. The novel delivery device and stented heart valve allows the surgeon to perform heart valve replacement on a beating heart.

Therefore, in accordance with one aspect of the disclosure a delivery device for a stented heart valve is received, the delivery device including a handle; an inner catheter shaft extending from the handle and having an enlarged bumper element at a distal end; an outer catheter shaft extending from the handle and slidably coupled around the inner catheter shaft, the outer catheter shaft including a generally cylindrical housing at a distal end that is structured to receive the bumper element therein; and a retraction mechanism for controlling longitudinal movement of the outer catheter shaft relative to the inner catheter shaft.

In a further aspect of the disclosure a method of transapically delivering a stented heart valve to an implantation site is provided including the steps of receiving a delivery device including a stationary inner catheter shaft, a retractable outer catheter shaft, and a generally cylindrical housing at a distal end of the outer catheter shaft; loading a crimped stented heart valve into the housing, the stented heart valve having a control suture that is engaged by an engagement mechanism of the delivery device to apply tension to the control suture and retain the stented heart valve in a crimped configuration; transapically inserting the delivery device into a heart and positioning the housing at an implantation site; retracting the outer catheter shaft relative to the inner catheter shaft to expose the stented heart valve within the implantation site; and manipulating the engagement mechanism to release tension from the control suture to allow for expansion within the implantation site.

In a further aspect of the disclosure, a method of transapically delivering a heart valve to an implantation site in a beating heart is provided including the steps of receiving a delivery device including a stationary inner catheter shaft, a retractable outer catheter shaft, and a generally cylindrical housing at a distal end of the outer catheter shaft; loading a crimped stented heart valve including a plurality of leaflets into the housing, the stented heart valve having a control suture that is engaged by an engagement mechanism of the delivery device to apply tension to the control suture and retain the stented heart valve in a crimped configuration; transapically inserting the delivery device into a heart and positioning the housing at an implantation site; retracting the outer catheter shaft relative to the inner catheter shaft to partially expose the stented heart valve within the implantation site; allowing expansion of the heart valve leaflets of the heart valve to stop backflow from an aorta; and manipulating the engagement mechanism to release tension from the control suture to allow for expansion within the implantation site.

BRIEF DESCRIPTION OF THE DRAWINGS

FIGS. 3A and 3B are front and back views, respectively, of the crimping tool of FIG. 1 illustrating a compression assembly in an uncrimped position.

FIGS. 12A and 12B are perspective and side views, respectively, of a stented heart valve that may be crimped and delivered to a patient in accordance with the present disclosure.

FIGS. 13A and 13B are perspective views of a delivery device in accordance with the present disclosure illustrating a housing in a refracted position and an extended position, respectively.

FIG. 13C is a partial perspective view of the delivery device illustrating a retraction mechanism.

FIGS. 14A and 14B are diagrams illustrating the operation of a delivery device engagement mechanism in accordance with the present disclosure.

DETAILED DESCRIPTION

The present disclosure is generally directed to devices and methods for reducing the size of a stented heart valve and delivering the stented heart valve to an implantation site for deployment within a patient. In some embodiments as described in detail herein, a stented heart valve may be crimped using a crimping tool, loaded into a delivery device, and deployed within a patient implantation site in a controlled manner.

As will be appreciated by those of ordinary skill in the art, the stented heart valve may be crimped or radially compressed in any suitable manner prior to loading the heart valve into the delivery device. Thus, the specific crimping tool embodiments set forth herein are provided merely for purposes of example and not limitation.

Figure 1:
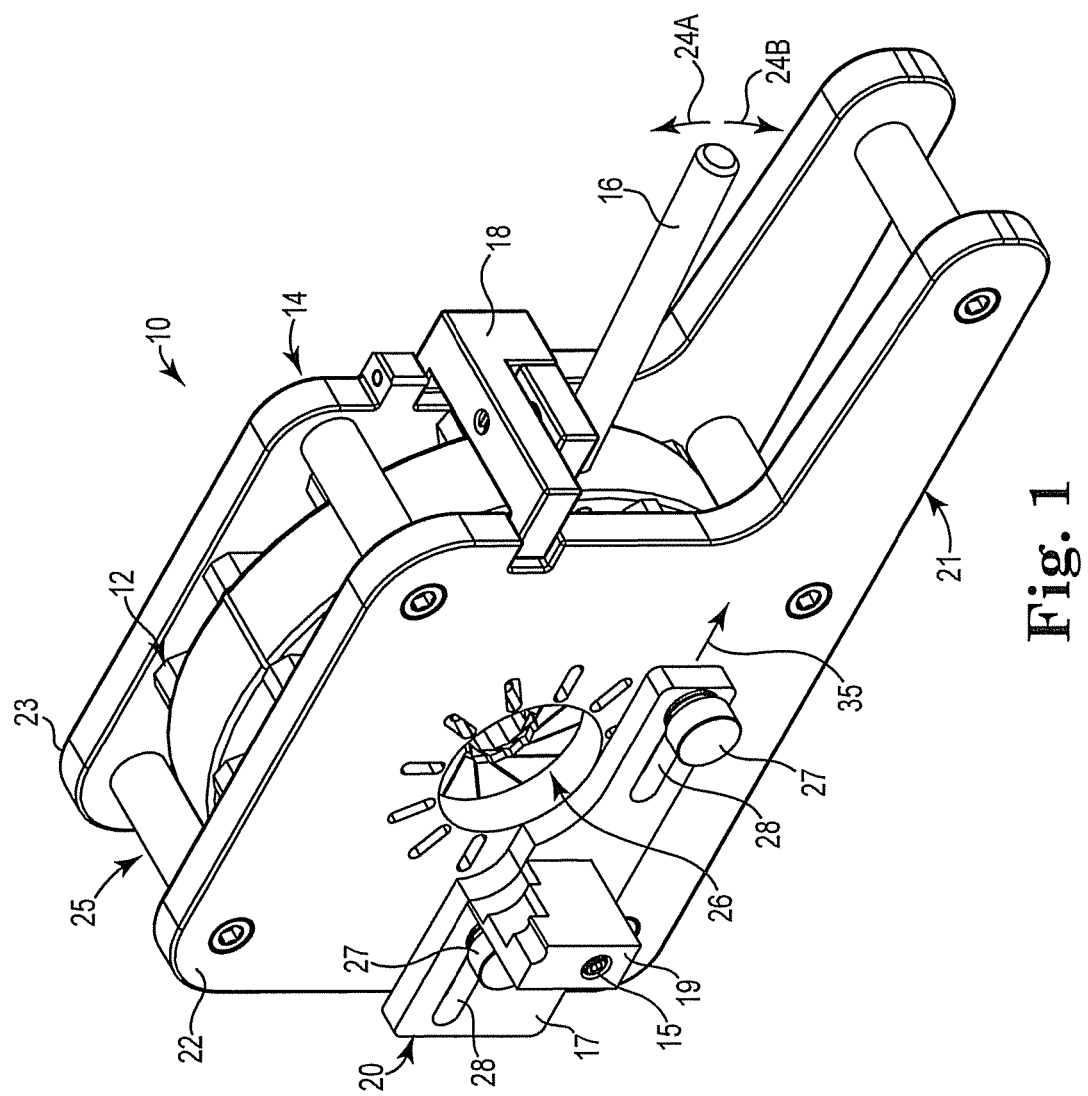
FIG. 1 is a perspective view of a crimping tool in accordance with the present disclosure.

FIG. 1 is a perspective view of one embodiment of a crimping tool 10 that may be utilized with the present disclosure. As illustrated in FIG. 1, the crimping tool 10 generally includes a compression assembly 12 disposed within a housing 14, an actuation lever 16, a lever lock 18, and a delivery device holder 20. The housing 14 includes an elongated base portion 21 that is sized and structured to provide sufficient support and stability to the crimping tool 10 during use. As will be appreciated by those of ordinary skill in the art, the base portion 21 of the housing 14 may be positioned on or attached to a table or other support surface during use of the crimping tool 10. In alternative embodiments, the base portion 21 may be a separate structure that is coupled to the housing 14 instead of being formed integral therewith.

As illustrated in FIG. 1, the housing 14 of the crimping tool 10 includes a front wall or plate 22 and a back wall or plate 23 coupled together in a spaced apart relationship so as to define an opening 25 therebetween. The compression assembly 12 is disposed between the front plate 22 and the back plate 23 and is operably coupled to the actuation lever 16 such that the actuation lever 16 extends through the opening 25. As will be discussed in further detail to follow, movement of the actuation lever in the directions indicated by arrows 24A and 24B controls movement of the compression assembly 12 between an uncrimped position and a crimped position, respectively. The actuation lever 16 of FIG. 1 is designed for manual operation by an operator, such as by grasping and moving the actuator 16 by hand. However, alternative embodiments of the crimping tool 10 may include actuation levers that are operated via alternative mechanical, electrical, hydraulic, electromechanical, or computer-controlled actuation means without departing from the intended scope of the present disclosure.

The housing 14 of the crimping tool 10 is described as being formed by two spaced apart plates that are coupled together so as to form an opening therebetween merely for purposes of example and not limitation. Thus, numerous other housing configurations may be used as will be appreciated by those of ordinary skill in the art. In one alternative embodiment, the housing 14 may instead be formed as a rear housing portion having a cavity that is structured to receive the compression assembly 12 and a cover plate that may be coupled to the rear housing portion such that the compression assembly 12 is substantially enclosed therein. Furthermore, the housing 14 may be constructed using any suitable materials including, but not limited to, various metals or plastics.

Although not a necessary component of the present disclosure, the lever lock 18 is hingedly coupled to the housing 14 and operable to lock the actuation lever 16 when the compression assembly 12 is in the crimped position. As illustrated in FIG. 1, the lever lock 18 "blocks" movement of the actuation lever 16 in the direction indicated by arrow 24A thereby preventing unintentional expansion of the compression assembly 12 and the stent (not shown) positioned therein from the crimped position back toward the uncrimped position. As discussed above, repeated cycles of compression and expansion of a stent may lead to fatigue or weakening of the stent structure. Thus, the lever lock 18 may be used to ensure that the stent is only crimped a single time prior to delivery to a patient.

The delivery device holder 20 is structured to engage a delivery device and align the delivery device with an access aperture 26 in the front plate 22 of the housing 14 that is sized to allow a stent (not shown) to be passed therethrough and into the compression assembly 12 for crimping. This alignment allows the crimped stent to be loaded into the delivery device for subsequent delivery to a patient. More particularly, as illustrated in FIG. 1 the delivery device holder 20 includes a sliding plate 17 having a seat member 19 that is structured to mate with or engage the delivery device. As will be appreciated by those of ordinary skill in the art, the structure and contour of the seat member 19 may vary depending upon the type of delivery device that is being supported. The sliding plate 17 and the seat member 19 are illustrated in FIG. 1 as separate components that are coupled together with a suitable fastening means such as a fastener 15. Alternatively, the sliding plate 17 and the seat member 19 may be formed as a single, integral unit.

The sliding plate 17 is slidably coupled to the front plate 22 of the housing 14 via at least one engagement member 27 positioned within a corresponding horizontal slot 28. The delivery device holder 20 is structured for movement in the direction indicated by arrow 35 from a first position as illustrated in FIG. 1 wherein the seat member 19 is not aligned with a center axis of the access aperture 26 to a second position wherein the seat member 19 is substantially aligned with the center axis of the access aperture 26. The range of movement of the delivery device holder 20 is determined by the length of the horizontal slot 28 in the sliding plate 17.

The delivery device holder 20 of FIG. 1 is illustrated as including two engagement members 27 and two corresponding horizontal slots 28 merely for purposes of example and not limitation. Those of ordinary skill in the art will appreciate that any number of engagement members and corresponding slots may be used without departing form the intended scope of the present disclosure.

Figure 2:
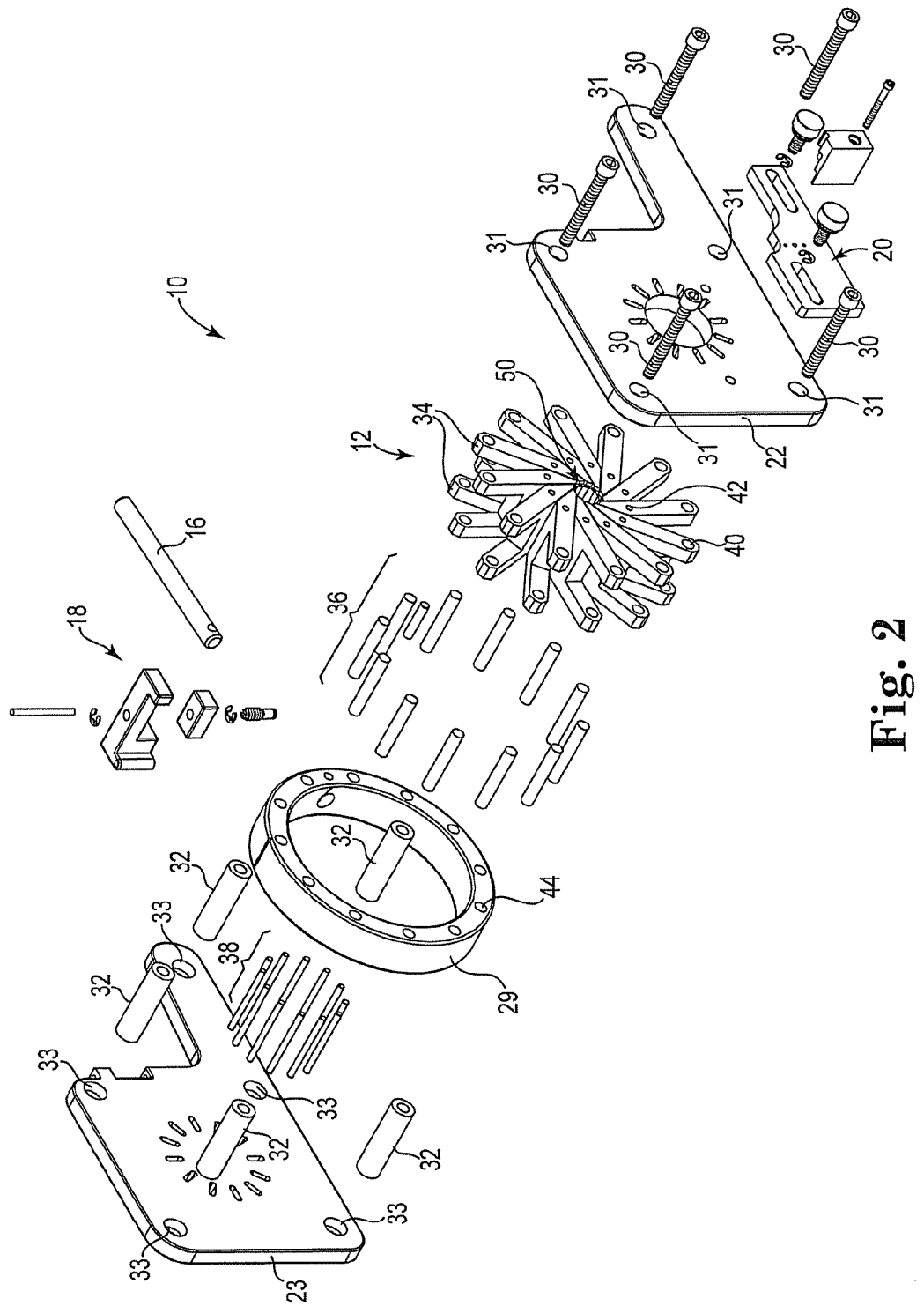
FIG. 2 is an exploded perspective view of the crimping tool of FIG. 1.

FIG. 2 is an exploded perspective view of the crimping tool 10 of FIG. 1. As illustrated in FIG. 2, the crimping tool 10 further includes a drive wheel 29 that, along with the compression assembly 12, is structured to be positioned between the front plate 22 and the back plate 23 of the housing 14. The drive wheel 29 is a generally cylindrical structure with an open center portion, thereby resembling a rim or ring member. The drive wheel 29 is rotatable with respect to the housing 14 and operably coupled to the compression assembly 12 to drive movement of the compression assembly 12 during the crimping process. As will be appreciated by those of ordinary skill in the art, the front plate 22 and the back plate 23 are spaced sufficiently apart when assembled (FIG. 1) such that the drive wheel 29 and attached compression assembly 12 may freely rotate therebetween. The actuation lever 16 is designed to operably engage the drive wheel 29 to initiate and control the movement of the drive wheel 29. As will be appreciated by those of ordinary skill in the art, the actuation lever 16 may be coupled to the drive wheel 29 in any suitable manner, or alternatively may be formed integral with the drive wheel 29.

With the crimping tool 10 illustrated in FIG. 2, the front plate 22 is attachable to the back plate 23 with a plurality of fasteners 30 that are structured to be passed though corresponding pluralities of apertures 31 in the front plate 22, elongate spacer elements 32 positioned between the front plate 22 and the back plate 23, and apertures 33 in the back plate 23. The fasteners 30 may have external threads that are structured to engage with internal threads of the apertures 31 in the front plate 22 and/or the apertures 33 in the back plate 23. As will be appreciated by those of ordinary skill in the art, numerous other means for attaching the front plate 22 to the back plate 23 of the housing 14 are contemplated and within the intended scope of the present disclosure including, but not limited to, rivets, welding, an adhesive, or the like. Thus, threaded fasteners are described and illustrated merely for purposes of example and not limitation.

As illustrated in FIG. 2, the compression assembly 12 includes a plurality of bars 34, a plurality of drive pins 36, and a plurality of guide pins 38. The drive pins 36 and guide pins 38 are preferably metallic and generally cylindrical in shape, although the pins may be constructed in various other shapes and from various other materials without departing from the intended scope of the present disclosure. Each of the bars 34 includes a generally cylindrical drive pin slot 40 structured to receive one of the drive pins 36 and a generally cylindrical guide pin slot 42 structured to receive one of the guide pins 38. The drive wheel 29 includes a plurality of generally cylindrical drive wheel slots 44 that are structured to receive the drive pins 36 to operably couple the drive wheel 29 to the plurality of bars 34 of the compression assembly 12. The drive pin slots 40 and/or the drive wheel slots 44 may be sized such that they have a diameter that is slightly larger than the diameter of the drive pins 36 to allow the bars 34 to rotate or pivot with respect to the drive wheel 29 as the drive wheel is rotated with the actuation lever 16. The guide pin slots 42 may be sized similar to the guide pins 38 such that a friction fit is formed therebetween, or alternatively the guide pin slots 42 may be sized larger than the guide pins 38 to allow for slight rotation of the distal end of the bars 34.

The crimping tool 10 is described and illustrated herein as including a single plurality of drive pins 36 and a single plurality of guide pins 38 merely for purposes of example and not limitation. In alternative embodiments, the compression assembly 12 may include a first plurality of drive pins structured to extend from the drive wheel slots 44 toward the front side of the bars 34 adjacent the front plate 22 and a second plurality of drive pins structured to extend from an opposite end of the drive wheel slots 44 toward the back side of the bars 34 adjacent the back plate 23. Similarly, the compression assembly 12 may include a first plurality of guide pins structured to extend from the guide pin slots 42 in the bars 34 toward the front plate 22 and a second plurality of guide pins structured to extend from an opposite end of the drive pin slots 42 in the bars 34 toward the back plate 23.

The drive wheel slots 44 may be substantially equally spaced around the circumference of the drive wheel 29. Furthermore, as illustrated in FIG. 2 the number of drive wheel slots 44 is equal to the number of bars 34 in the compression assembly 12. Thus, each bar 34 includes one drive pin slot 40, one guide pin slot 42, and is associated with one drive wheel slot 44 in the drive wheel 29. With embodiments in which the drive wheel slots 44 are equally spaced around the circumference of the drive wheel 29, the bars 34 are also equally spaced around the circumference of the drive wheel 29 in a spoke-like fashion.

As will be described in further detail to follow, the bars 34 are arranged to form a generally circular or polygonal chamber 50 that is structured to receive a stent (not shown) or other element to be crimped. With the stent positioned within the chamber 50, the internal dimensions of the chamber 50 may be reduced by manipulating the actuation lever 16 as previously discussed, thereby moving the compression assembly 12 from an uncrimped position to a crimped position. The extent to which the dimensions of the chamber 50 are reduced, and thus the amount of crimping, may be controlled by the position of the actuation lever 16. In the embodiment of the crimping tool 10 illustrated herein, the actuation lever 16 moves in a clockwise direction during the crimping process. However, those of ordinary skill in the art will appreciate that the compression assembly 12 may be modified such that the actuation lever 16 instead moves in a counter-clockwise direction during the crimping process.

Figure 3B:
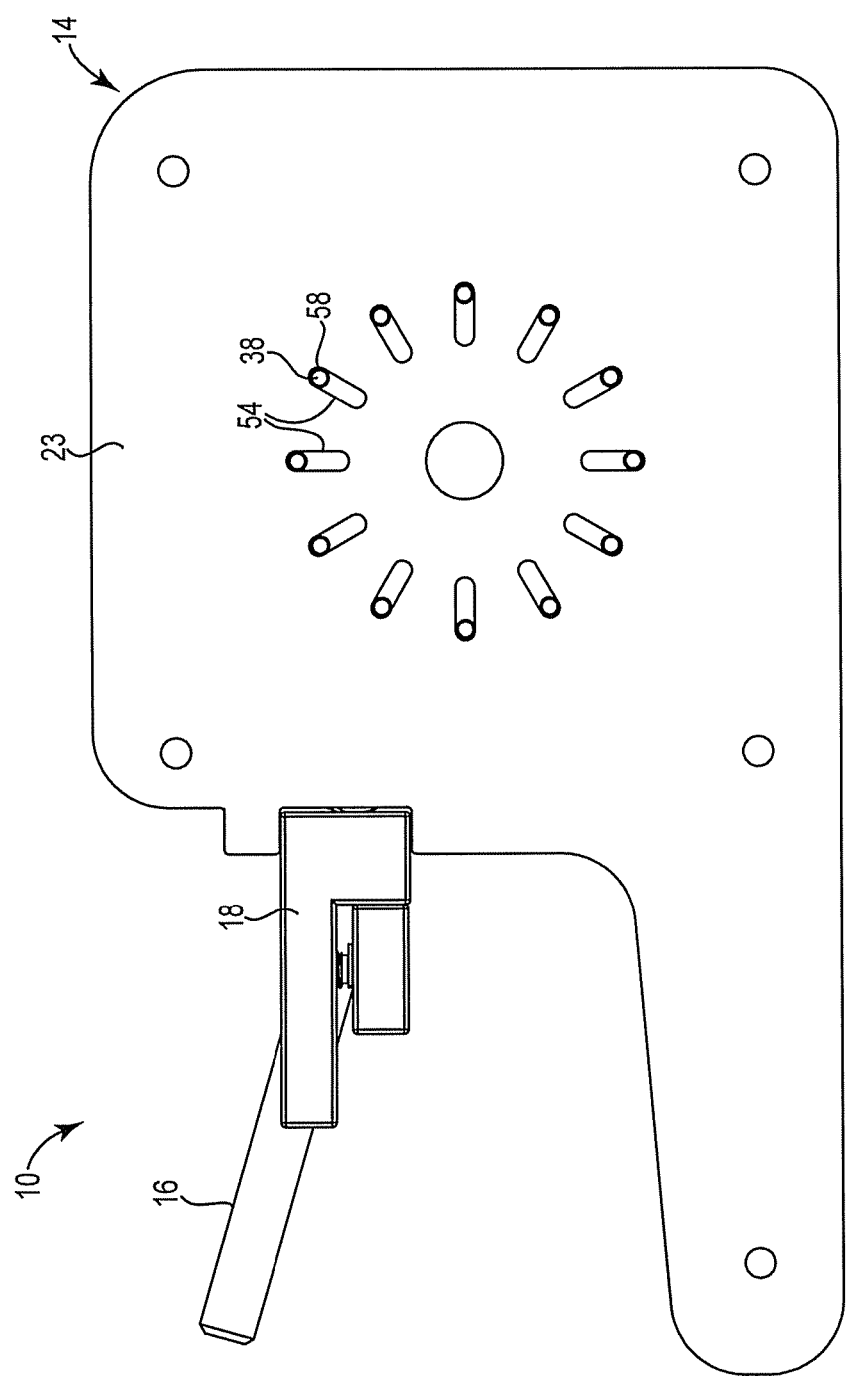

FIGS. 3A and 3B are front and back views, respectively, of the crimping tool 10 in accordance with the present disclosure. As illustrated in FIG. 3A, the front plate 22 of the housing 14 includes a first plurality of radially extending elongate slots 52. Similarly, as illustrated in FIG. 3B, the back plate 23 of the housing 14 includes a second plurality of radially extending elongate slots 54 that are aligned with the first plurality of elongate slots 52. When assembled, each of the guide pins 38 is structured to pass through a corresponding guide pin slot 42 in one of the bars 34 as previously discussed. Additionally, each of the guide pins 38 is designed with a length that is sufficient to allow a first end of the guide pin 38 to extend into a corresponding one of the elongate slots 52 in the front plate 22 and a second end of the guide pin 38 to extend into a corresponding one of the elongate slots 54 in the back plate 23. As will be appreciated by those of ordinary skill in the art, the elongate slots 52 and 54 are structured and sized to allow a predetermined amount of radial movement of the guide pins 38 and attached bars 34 during the crimping process to alter the dimensions of the chamber 50.

Figure 4A:
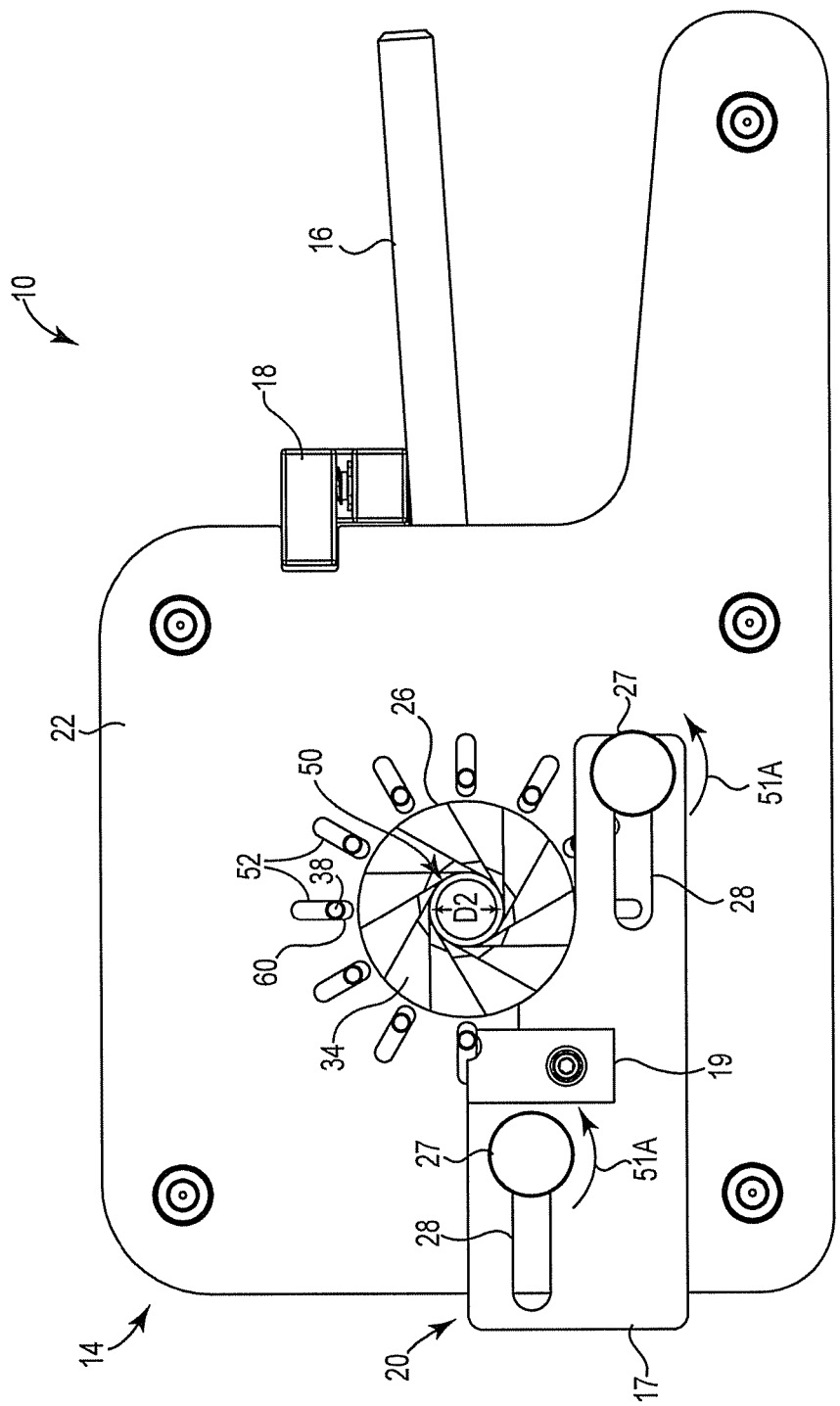
FIGS. 4A and 4B are front and back views, respectively, of the crimping tool of FIG. 1 illustrating the compression assembly in a crimped position.
Figure 4B:
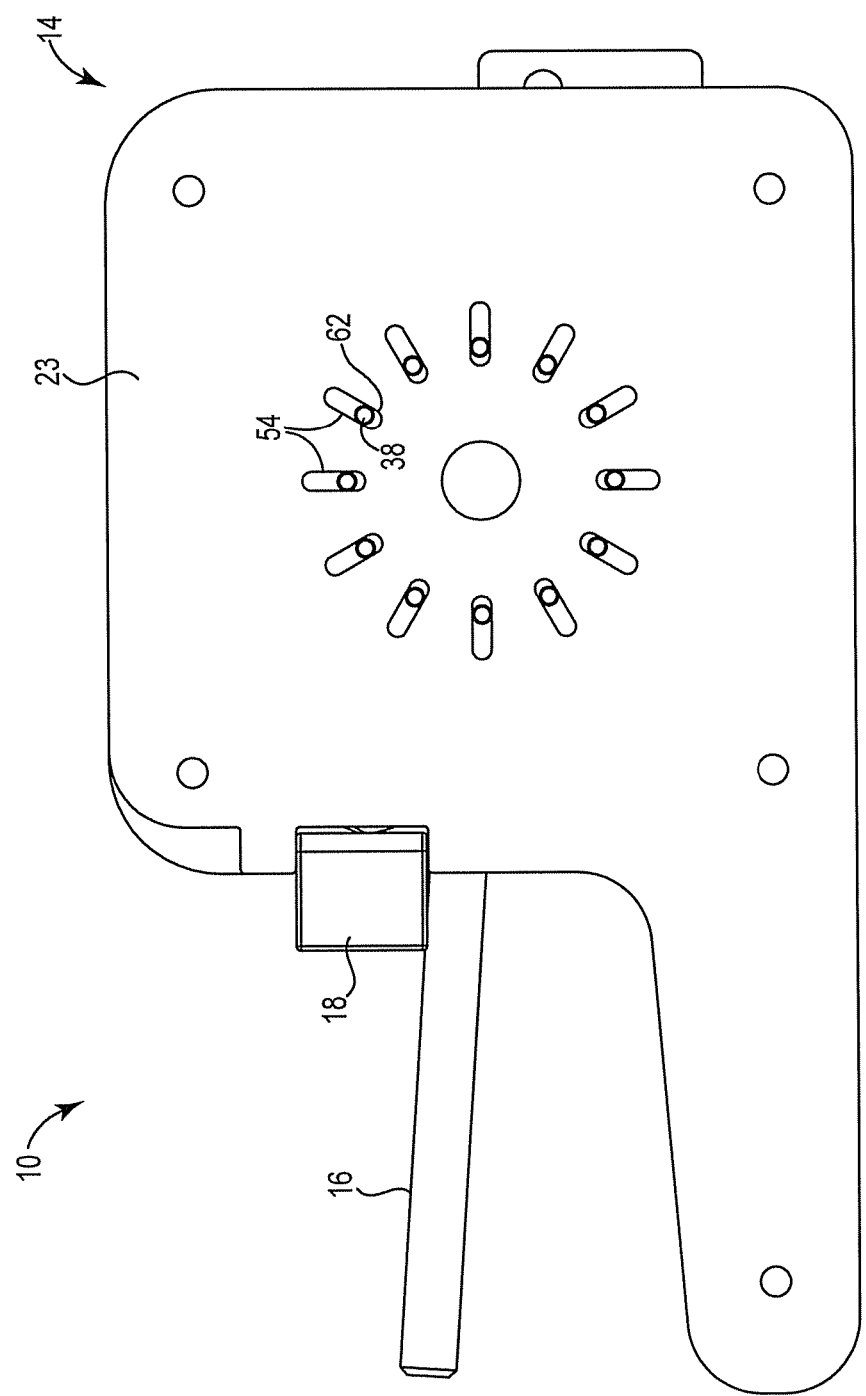

In the state of FIGS. 3A and 3B, the compression assembly 12 is in an "uncrimped" position. FIGS. 4A and 4B are front and back views, respectively, of the crimping tool 10 illustrating the compression assembly 12 in a "crimped" position. As will be appreciated by those of ordinary skill in the art, the uncrimped position of FIGS. 3A and 3B and the crimped position of FIGS. 4A and 4B represent the two endpoints of the crimping range. Depending upon the size of the stent (not shown) and the amount of crimping that is desired, an operator may achieve a desirable amount of crimping without actuating the compression assembly 12 to the fully crimped position of FIGS. 4A and 4B.

With reference again to the uncrimped position of FIG. 3A, the chamber 50 is defined by a first internal dimension D1, which may approximately represent the diameter of a circle. When the chamber 50 is in the uncrimped position, each of the guide pins 38 is positioned substantially adjacent to a first end 56 of a corresponding elongate slot 52 in the front plate 22 as illustrated in FIG. 3A and a first end 58 of a corresponding elongate slot 54 in the back plate 23 as illustrated in FIG. 3B. In order to commence the crimping process to decrease the internal diameter D1 of the chamber 50, the operator may move the actuation lever 16 in the direction indicated by arrow 24B.

As illustrated in the crimped position of FIG. 4A, the chamber 50 is defined by a reduced second internal dimension D2, which may also approximately represent the diameter of a circle. As will be appreciated by those of ordinary skill in the art, a center axis of the chamber 50 corresponds with the center axis of the access aperture 26. When the chamber 50 is in the crimped position, each of the guide pins 38 is positioned substantially adjacent to a second end 60 of a corresponding elongate slot 52 in the front plate 22 as illustrated in FIG. 4A and a second end 62 of a corresponding elongate slot 54 in the back plate 23 as illustrated in FIG. 4B. As the chamber 50 contracts and becomes smaller, the internal surface defining the chamber 50 moves toward the center axis of the chamber 50 in a substantially uniform manner such that the chamber maintains a substantially circular configuration throughout the crimping process. This uniform compression is the result of the interaction between the bars 34, the drive pins 36, the guide pins 38, and the elongate slots 52 and 54 in the housing 14.

More specifically, during the crimping process, movement of the actuation lever 16 in the clockwise direction 24B causes the drive wheel 29 to also move in the clockwise direction. Because the bars 34 of the compression assembly 12 are operably coupled to the drive wheel 29 with the drive pins 36 at a proximal end, the proximal ends of the bars 34 are caused to rotate clockwise along with the drive wheel 29. As discussed above, in order to allow movement of the bars 34 relative to one another to adjust the size of the chamber 50, the drive pins 36, drive pin slots 40, and drive wheel slots 44 are sized such that the bars 34 are rotatable or pivotable with respect to the drive wheel 29 along an axis through the drive pins 36. However, the distal ends of the bars 34 are constrained from any substantial amount of rotation due to the engagement of the guide pins 38 with the elongate slots 52 in the front plate 22 and the elongate slots 54 in the back plate 23. As a result, the guide pins 38 are allowed to slide inward along the radially extending elongate guide slots 52 and 54 to reduce the internal diameter of the chamber 50.

As will be appreciated by those of ordinary skill in the art, any radially compressible stent having a diameter in the expanded state that is greater than D2 but less than D1 may be crimped with the crimping tool 10 of the present disclosure. Furthermore, the size of the chamber 50 in the uncrimped and crimped positions may be modified by changing, for example, the number, size, or shape of the bars 34 of the compression assembly 12.

As illustrated in FIGS. 3A and 4A, the delivery device holder 20 is located in the first position wherein the seat member 19 is not aligned with the center axis of the access aperture 26. Once the stent (not shown) or other device has been crimped within the chamber 50, the seat member 19 of the delivery device holder 20 may be substantially aligned with the center axis of the access aperture 26 by moving the sliding plate 17 to the position illustrated in FIG. 5. With the seat member 19 of the delivery device holder 20 substantially aligned with the center axis of the access aperture 26, the crimped stent may be easily loaded into the delivery device for subsequent deployment within a patient.

Figure 5:
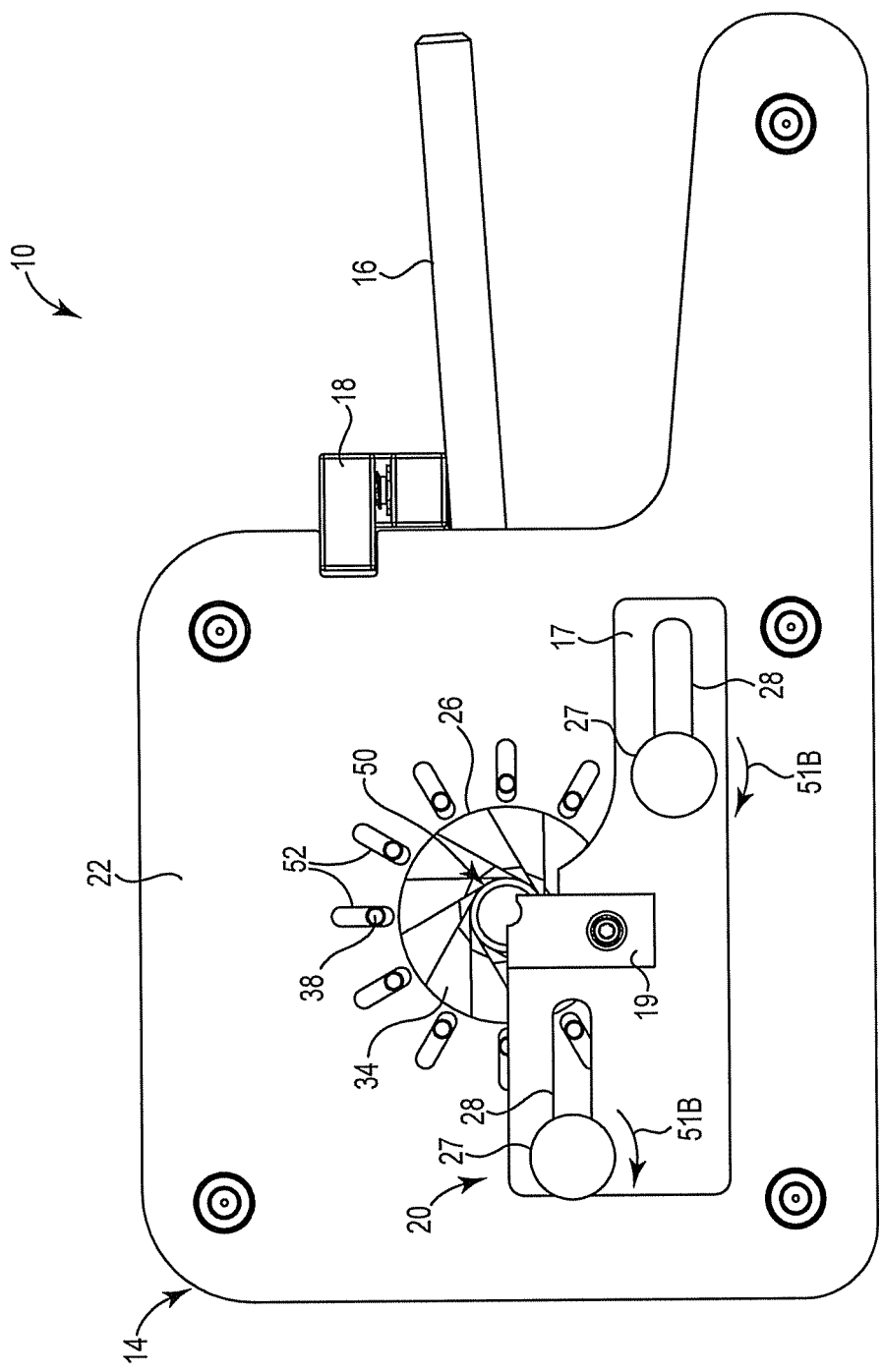
FIG. 5 is a front view of the crimping tool of FIG. 1 illustrating a delivery device holder having a seat member aligned with an access aperture of the crimping tool.

In the embodiment of the delivery device holder 20 illustrated herein, the engagement members 27 are externally threaded fasteners that are structured to threadably engage apertures in the front plate 22 of the housing 14. More particularly, the engagement members 27 are movable from a locked position wherein a compression force is applied to the sliding plate 17 to maintain its position relative to the front plate 22 of the housing 14, to an unlocked position wherein the compression force is released and the sliding plate 17 is movable relative to the front plate 22. Prior to commencing movement of the sliding plate 17, the engagement members 27 are first rotated in a counterclockwise direction 51A as illustrated in FIG. 4A. Rotating the engagement members 27 in such a manner releases the compression force applied to the sliding plate 17. After releasing the compression force by moving the engagement members 27 from the locked to the unlocked position, the delivery device holder 20 may be slid to the position illustrated in FIG. 5 to substantially align the seat member 19 with the center axis of the access aperture 26. Once the seat member 19 has been properly aligned, the engagement members 27 may be rotated in a clockwise direction 51B as illustrated in FIG. 5 to prevent subsequent movement of the delivery device holder 20 relative to the front plate 22 of the housing 14.

Although movement of the delivery device holder 20 has been described as occurring after the compression assembly 12 has been actuated to the crimped position, those of ordinary skill in the art will appreciate that the seat member 19 may be aligned with the center axis of the access aperture 26 at any time without departing from the intended scope of the present disclosure. For example, the seat member 19 of the delivery device holder 20 may be aligned with the center axis of the access aperture 26 prior to actuating the actuation lever 16 to commence the crimping process.

FIGS. 6A-6D are perspective, side, top, and bottom views, respectively, of one of the bars 34 in accordance with the present disclosure. As illustrated in FIGS. 6A-6D, the bar 34 includes a proximal end 53, a distal end 55, a front face 70, a back face 72, a first side face 74, a second side face 76, and a chamfered leading edge 78. The first and second side faces 74 and 76 are substantially straight or planar surfaces that are generally parallel to one another. The second side face 76 opposes and intersects the chamfered leading edge 78 near the distal end 55. As further illustrated in FIGS. 6A-6D, a proximal portion of the bar 34 comprises a front leg 80A and a back leg 80B separated by a proximal opening 82 that is sized similar to or slightly larger than a width of the drive wheel 29. In the illustrated embodiment, the drive pin slot 40 extends through both the front leg 80A and the back leg 80B. However, in alternative embodiments, the drive pin slot 40 may extend completely through either the front leg 80A or the back leg 80B and only partially through the other of the front leg 80A or the back leg 80B as will be appreciated by those of ordinary skill in the art.

Although the distal end 55 is illustrated as comprising a substantially flat chamfered leading edge 78, the leading edge 78 may alternatively be structured with a non-flat, curvilinear, and/or rounded surface without departing from the intended scope of the present disclosure.

Figure 6A:
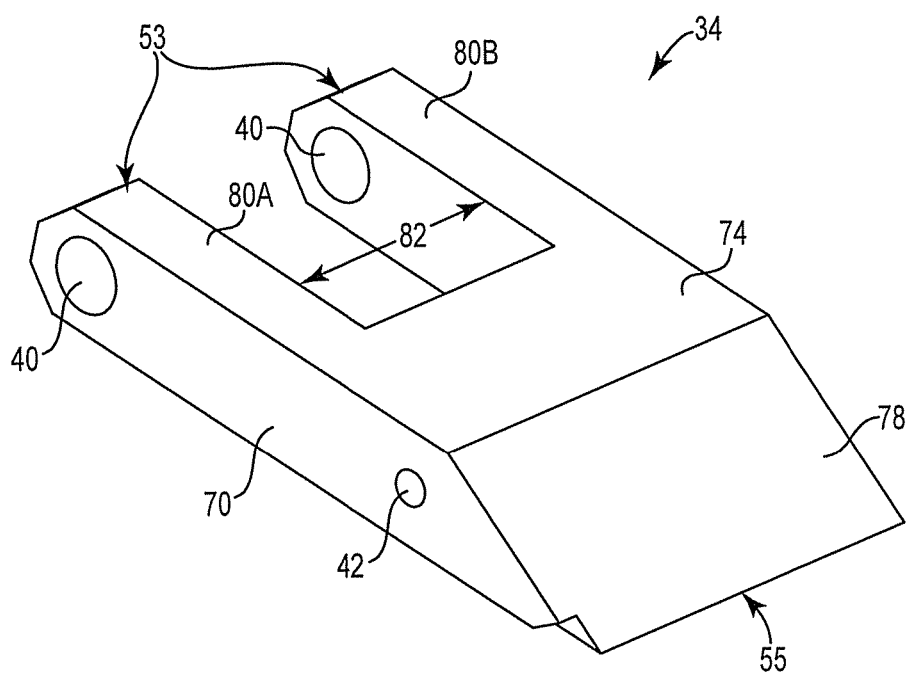
FIGS. 6A-6D are perspective, side, top, and bottom views, respectively, of a compression assembly bar in accordance with the present disclosure.
Figure 6B:
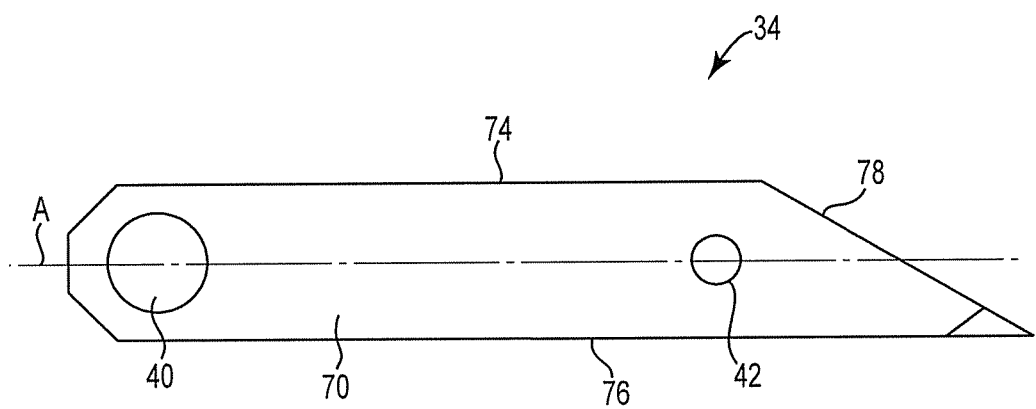
Figure 6C:
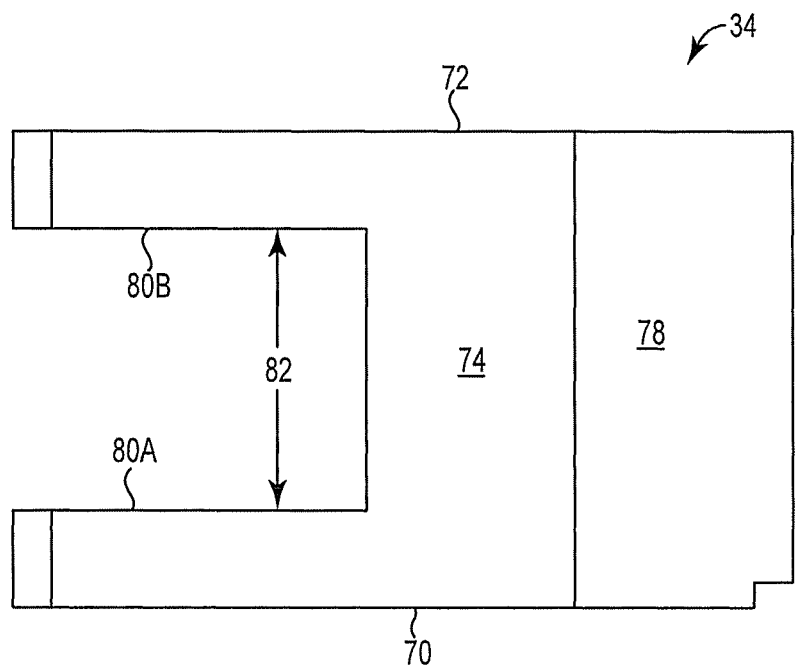
Figure 6D:
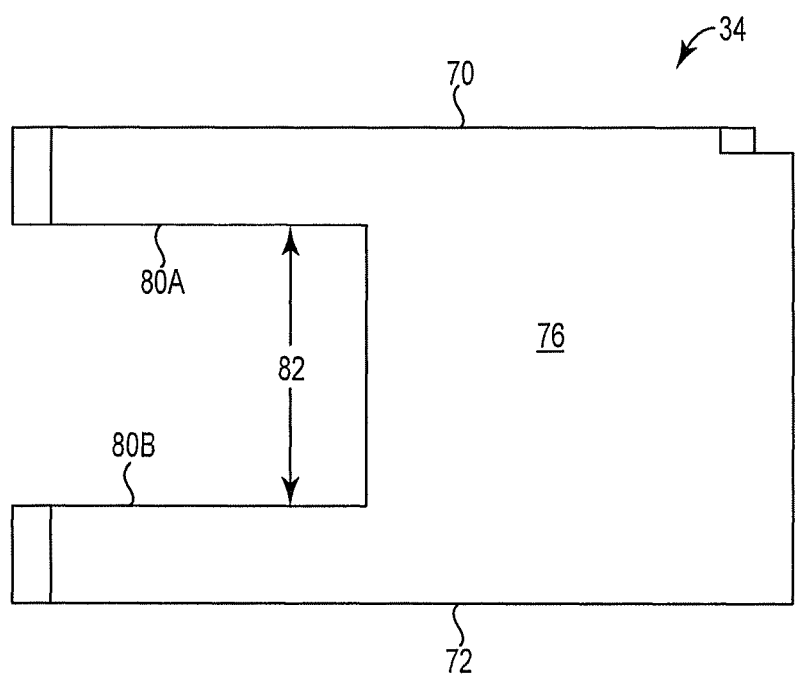

As illustrated in FIG. 6B, the centers of the drive pin slot 40 and the guide pin slot 42 are substantially aligned with a bar axis A extending through a center plane of the bar 34. However, in alternative embodiments, the drive pin slot 40 and/or the guide pin slot 42 may be offset from the bar axis A. As will be appreciated by those of ordinary skill in the art, offsetting the drive pin slot 40 and/or the guide pin slot 42 may provide additional tolerance for movement of the bars 34 through the crimping range of the compression assembly 12.

The bars 34 may be constructed using any suitable material as will be appreciated by those of ordinary skill in the art. Exemplary materials may include, but are not limited to, polymeric materials, polycarbonate materials, thermoplastic materials, ceramic materials, composite materials, metallic materials, and the like.

Figure 7:
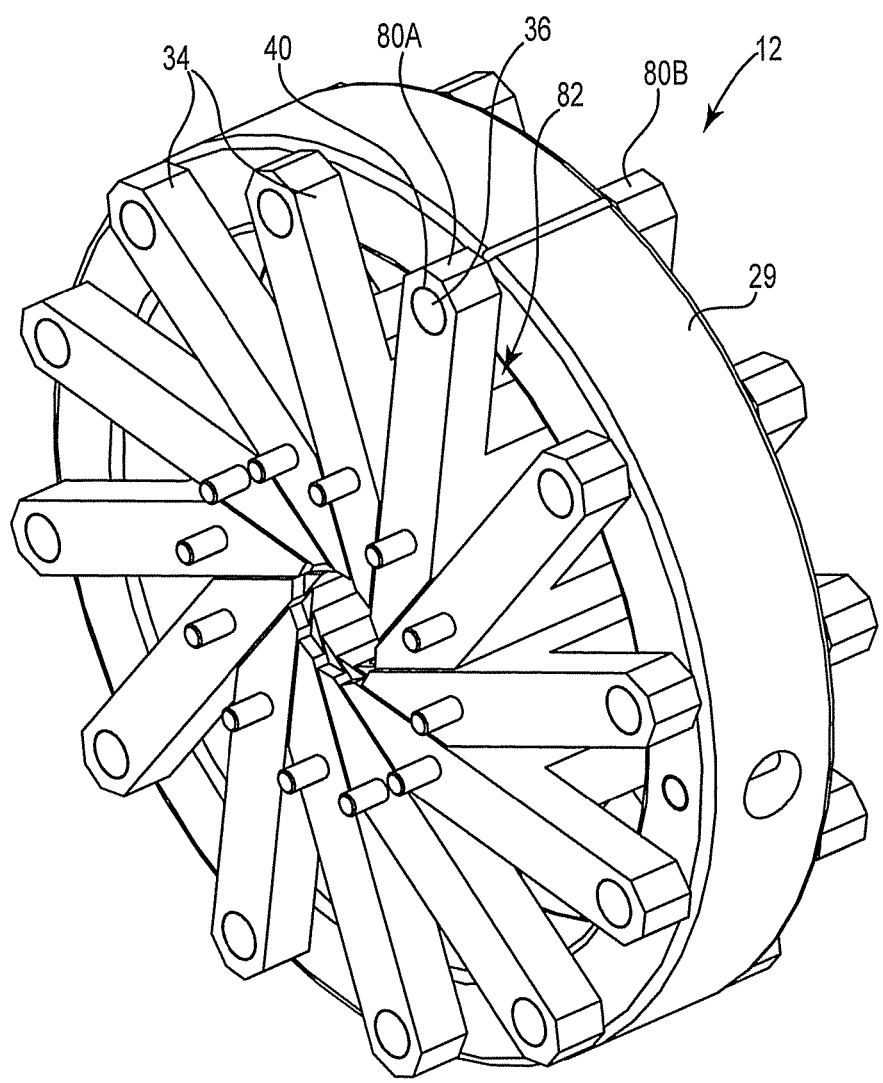
FIG. 7 is a perspective view of the compression assembly and attached drive wheel removed from the crimping tool.

FIG. 7 is a perspective view of the compression assembly 12 and the drive wheel 29 removed from the crimping tool to illustrate the positioning of the drive wheel 29 relative to the bars 34 of the compression assembly 12. As illustrated in FIG. 7, the drive wheel 29 is structured and sized to be positioned within the proximal opening 82 between the front leg 80A and the back leg 80B of the bars 34. As previously discussed, the compression assembly 12 is operably coupled to the drive wheel 29 by inserting the drive pin 36 through the drive pin slot 40 in the front and back legs 80A and 80B and the drive wheel slot 44 of the drive wheel 29 positioned therebetween.

Figure 8:
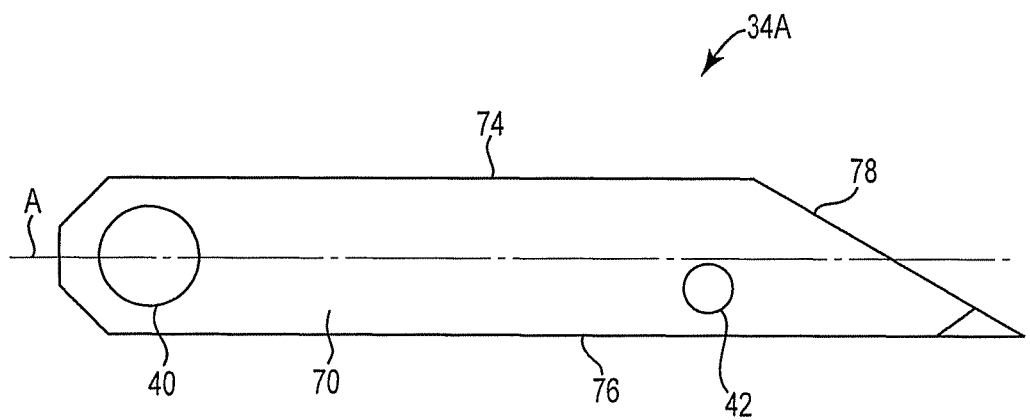
FIG. 8 is another embodiment of a compression assembly bar in accordance with the present disclosure.

FIG. 8 is a side view of an alternative embodiment bar 34A in accordance with the present disclosure. As illustrated in FIG. 8, the bar 34A is substantially similar to the bar 34 previously described in detail with reference to FIGS. 6A-6D. However, instead of the drive pin slot 40 and the guide pin slot 42 of the bar 34A being in substantial alignment with the bar axis A, the guide pin slot 42 of the bar 34A is offset from the bar axis A. As will be appreciated by those of ordinary skill in the art, the guide pin slot 42 may be offset in either direction, i.e. toward the first side face 74 or the second side face 76, without departing from the intended scope of the present disclosure.

Figure 9:
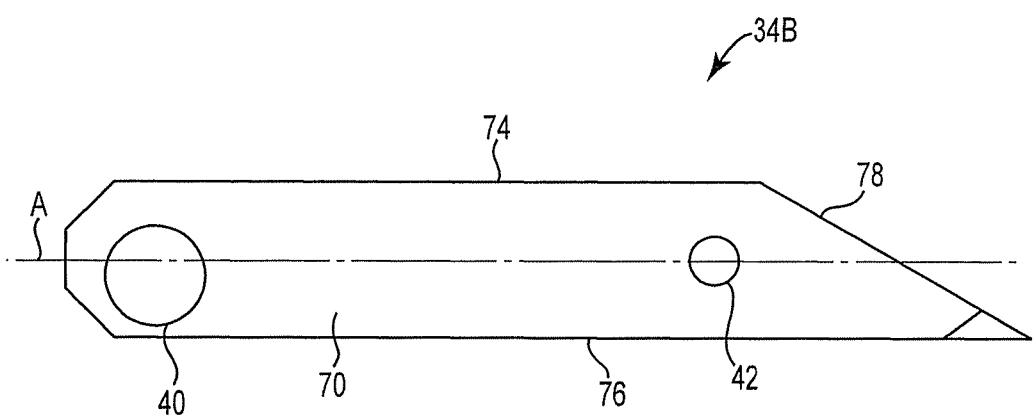
FIG. 9 is another embodiment of a compression assembly bar in accordance with the present disclosure.

FIG. 9 is a side view of another alternative embodiment bar 34B in accordance with the present disclosure. As illustrated in FIG. 9, the bar 34B is substantially similar to the bar 34 previously described in detail with reference to FIGS. 6A-6D. However, instead of the drive pin slot 40 and the guide pin slot 42 of the bar 34B being in substantial alignment with the bar axis A, the drive pin slot 40 of the bar 34B is offset from the bar axis A. As will be appreciated by those of ordinary skill in the art, the drive pin slot 40 may be offset in either direction, i.e. toward the first side face 74 or the second side face 76, without departing from the intended scope of the present disclosure.

Figure 10:
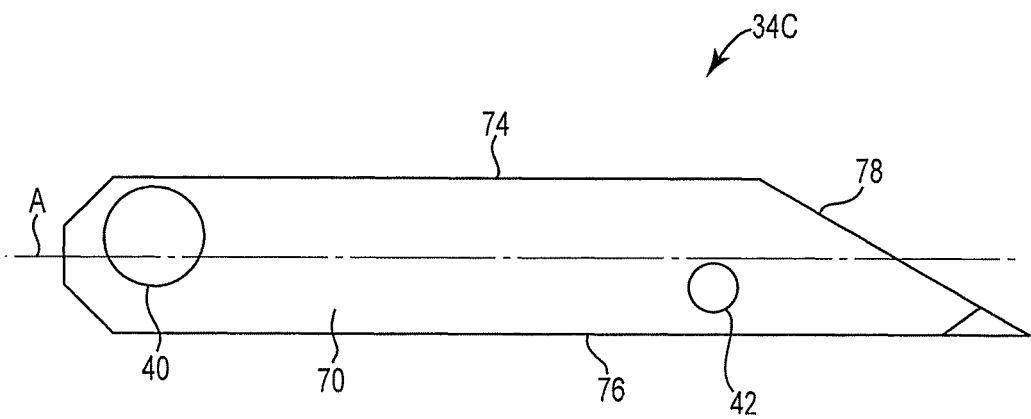
FIG. 10 is another embodiment of a compression assembly bar in accordance with the present disclosure.

FIG. 10 is a side view of another alternative embodiment bar 34C in accordance with the present disclosure. As illustrated in FIG. 10, the bar 34C is a "hybrid" of the bar 34A of FIG. 8 and the bar 34B of FIG. 9 wherein both the drive pin slot 40 and the guide pin slot 42 are offset from the bar axis A. As will be appreciated by those of ordinary skill in the art, the drive pin slot 40 and the guide pin slot 42 may either be offset on opposite sides of the bar axis A or on the same side of the bar axis A without departing from the intended scope of the present disclosure.

Figure 11A:
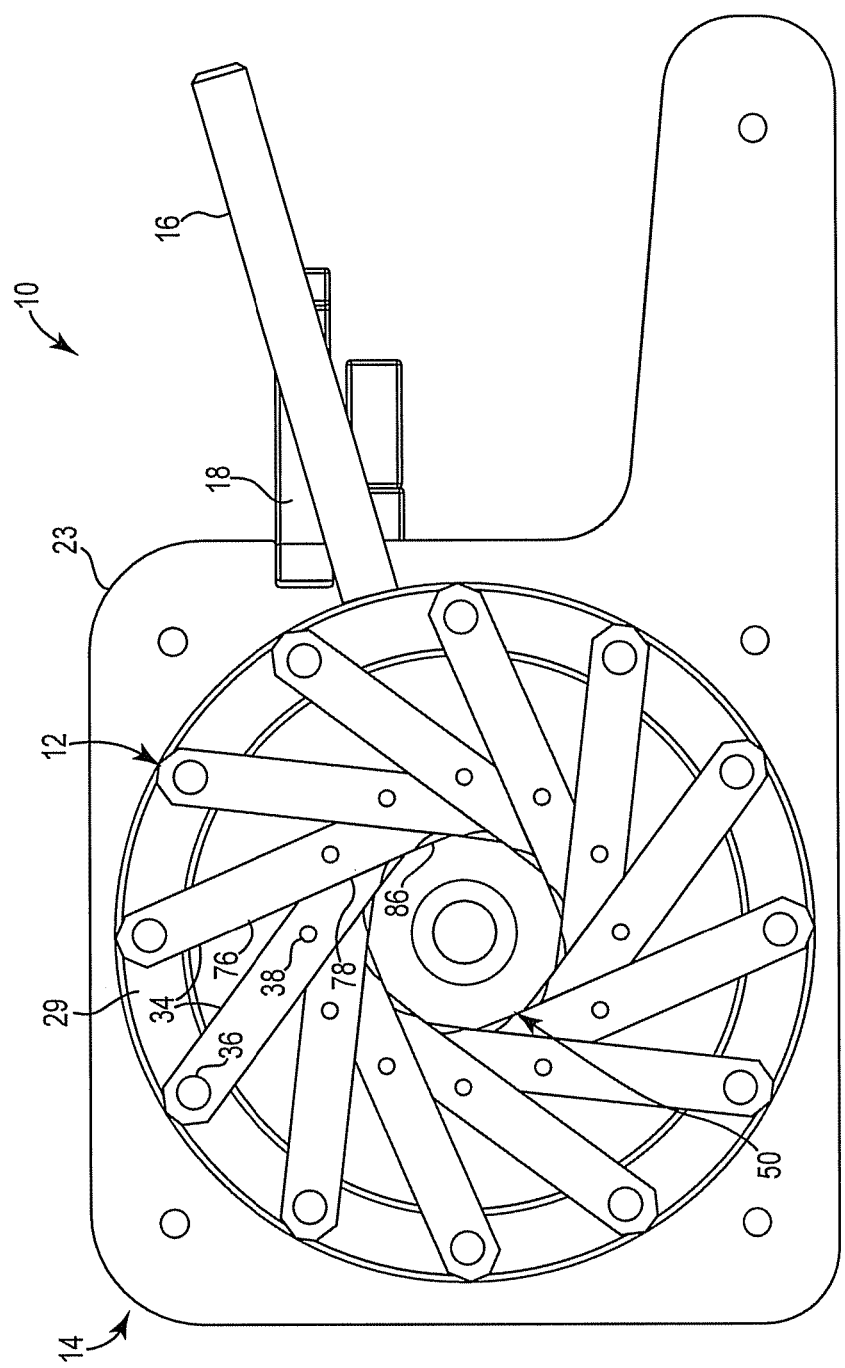
FIGS. 11A and 11B are front and back views, respectively, of the crimping tool of FIG. 1 with a front plate removed to illustrate movement of the compression assembly.

FIG. 11A is a front view of the crimping tool 10 with the front plate 22 (FIG. 2) removed illustrating the compression assembly 12 in the uncrimped position. As illustrated in FIG. 11A, the bars 34 are equally spaced around the drive wheel 29 and arranged such that the chamfered leading edge 78 of one bar 34 is slidable upon the second side face 76 of an adjacent bar 34 during the crimping process. Further, a perimeter of the chamber 50 is defined by an exposed portion 86 of the second side face 76 of each of the bars 34.

Figure 11B:
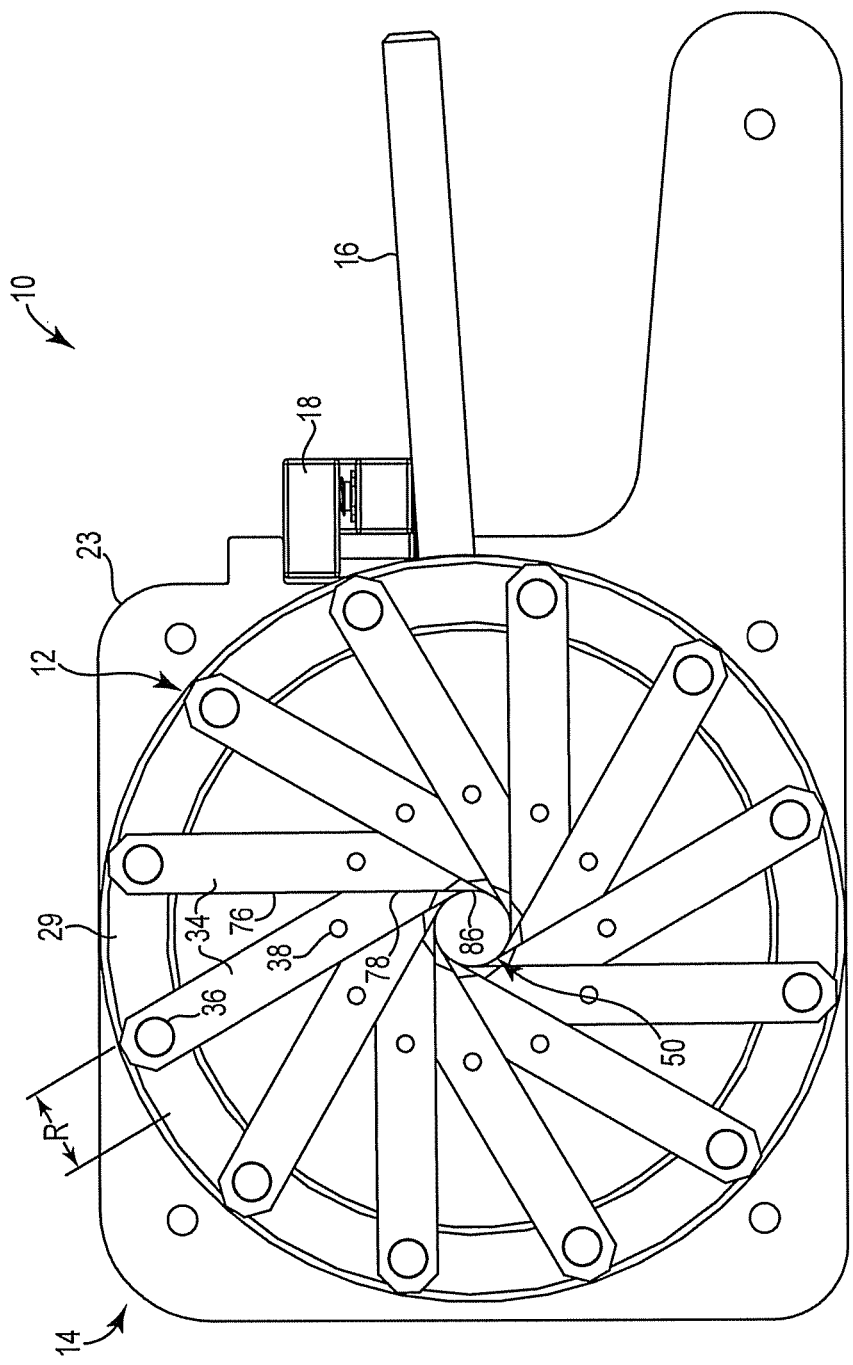

FIG. 11B is a front view of the crimping tool 10 with the front plate 22 (FIG. 2) removed illustrating the compression assembly 12 in the crimped position. As illustrated in FIG. 11B, the proximal ends of the bars 34 have rotated clockwise by a predetermined amount R relative to the uncrimped position. The distal ends of the bars 34 are constrained from any substantial amount of rotation due to the interaction of the guide pins 38 with the elongate slots 52 in the front plate 22 and the elongate slots 54 in the back plate 23 as previously discussed. Thus, the distal ends of the bars 34 are guided radially inward along the elongate guide slots 52 and 54 as the chamber 50 is contracted. As will be appreciated by those of ordinary skill in the art, in the crimped position illustrated in FIG. 11B there is a decrease in the size of the chamber 50 perimeter due to a reduction in the exposed portion 86 of the second side face 76 of each of the bars 34.

The compression assembly 12 is described and illustrated herein as including twelve bars 34. However, the number of bars 34 may be varied as will be appreciated by those of ordinary skill in the art. For example, the requisite number of bars 34 may depend upon a diameter of the drive wheel 29 or a width of the bars 34 between the first side face 74 and the second side face 76. Thus, twelve bars 34 are illustrated merely for purposes of example and not limitation.

Those of ordinary skill in the art will appreciate that the foregoing exemplary embodiment of a crimping tool is only one type of crimping tool that may be utilized with the transapical delivery tool and method of the present disclosure. Any tool that is capable of radially compressing a stented heart valve may also be used. One acceptable construction of a delivery device for transapically delivering a heart valve together with its method of use will now be described. The heart valve delivery device and method in accordance with the present disclosure allows for the loading and delivery of a radially compressible stented heart valve to a desired implantation position within a patient, such as the aortic annulus. The delivery device of the present disclosure allows the stented heart valve to be radially deployed in a controlled manner for precise anatomical placement.

FIGS. 12A and 12B are perspective and side views, respectively, of a stented heart valve 100 that may be crimped from a first enlarged sized to a second reduced size using the crimping tool 10 (FIG. 1) previously described or other crimping tools known to those skill in the art. As illustrated in FIGS. 12A and 12B, the stented heart valve 100 is a substantially tubular structure having a length L1 between an inflow end 102 and an outflow end 104 and generally includes a tri-leaflet replacement valve 106, a support stent 108, and an optional cloth covering 110 adjacent the inflow end 102. As will be appreciated by those of ordinary skill in the art, any suitable cloth material may be used such as polyester or the like. The replacement valve 106 is attached to the support stent 108 such that the replacement valve 106 resides therein. The support stent 108 is a radially expandable and collapsible structure adapted to be delivered to an implantation site such as an aortic annulus, and may be formed from any suitable material including, but not limited to, stainless steel or Nitinol.

The support stent 108 has a substantially tubular configuration and includes a plurality of longitudinally extending support posts 114 extending between an inflow rim and an outflow rim of the support stent 108. As illustrated in FIGS. 12A and 12B, the support stent 108 includes three support posts 114 corresponding to the three leaflets 115 of the replacement valve 106. The replacement valve 106 is secured to the support stent 108 by threading a plurality of commissural tabs 116 of the replacement valve 106 through slots in the support posts 114.

The replacement valve 106 is illustrated and described as a tri-leaflet valve merely for purposes of example and not limitation. Thus, the stented heart valve 100 may include a replacement valve having any number of valve leaflets. However, as will be appreciated by those of ordinary skill in the art, replacement valves having a number of leaflets other than three will require a different valve support structure.

As further illustrated in FIGS. 12A and 12B, the stented heart valve 100 includes a plurality of control sutures 112 that are sewn into the cloth covering 110 on the inflow side of the heart valve. Each control suture 112 is threaded through two suture apertures 118 in the cloth covering 110 formed on either side of the support posts. Thus, one control suture 112 is threaded through two suture apertures 118 positioned on either side of the support posts for a total of three control sutures 112. However, as will be appreciated by those of ordinary skill in the art, the number and location of the suture apertures 118 may vary without departing from the intended scope of the present disclosure so long as a sufficient number of suture apertures are utilized in order to maintain the radially compressed stented heart valve in the crimped configuration during deployment as will be described in detail to follow. For example, with regard to transapical delivery procedures, positioning three control sutures between the three support posts may give the surgeon an additional mechanical advantage when the valve is being positioned against the back flow of blood from the aorta.

FIG. 13A is a perspective view of a transapical delivery device 130 in accordance with the present disclosure. As illustrated in FIG. 13A, the delivery device 130 generally includes a handle 132 having a rotatable knob 131, an engagement mechanism 133 operably coupled to the handle 132, an outer catheter shaft 134 extending from the handle 132, and an inner catheter shaft 135 extending from the handle 132 and through the outer catheter shaft 134. The outer catheter shaft 134 and the inner catheter shaft 135 can be formed from a flexible or bendable material to allow the delivery device 130 to adapt to the path of the access aperture in the heart during valve delivery. The distal end of the inner catheter shaft 135 includes an end piece 137 that is structured as a bumper element for contacting the stented heart valve 100 (FIG. 12A) as the outer catheter shaft 134 is retracted relative to the inner catheter shaft 135 to deliver the stented heart valve 100 as will be described in further detail to follow. The outer catheter shaft 134 includes a generally cylindrical housing 136 at a distal end that is sized and shaped to extend over the end piece 137 and the stented heart valve 100 to define a stent chamber for delivery of the stented heart valve 100.

The outer catheter shaft 134 is operatively connected to the knob 131 via an externally threaded sleeve 140 to effect longitudinal movement of the outer catheter shaft 134 and the housing 136 relative to the inner catheter shaft 135 upon rotation of the knob 131. Thus, the knob 131 and the externally threaded sleeve 140 together form a retraction mechanism 141. As a point of reference, FIG. 13A illustrates a retracted position of the housing 136, while FIG. 13B illustrates a perspective view of the delivery device 130 with the housing 136 in an extend position. When the housing 136 is in the extended position of FIG. 13B, the housing 136 defines a generally cylindrical housing lumen 138 that is sized and structured to receive the stented heart valve 100 (FIG. 12A) therein upon crimping. In the extended housing position, the housing lumen 138 has a length L2 between the end piece 137 and a distal edge 139 of the housing 136 that is substantially equivalent (e.g., within 5%) to the length L1 (FIG. 12B) of the stented heart valve 100 such that the outflow end 104 (FIG. 12A) can be positioned substantially adjacent to the distal edge 139 of the housing 136 during deployment so that the surgeon can ensure correct anatomical placement. As appreciated by those of ordinary skill in the art, the length L2 of the housing lumen 138 may alternatively be greater than or less than the length L1 of the stented heart valve 100 without departing from the intended scope of the present disclosure. Further, because there is much less room to maneuver a delivery device that is placed transapically as opposed to surgically via an open-chest procedure, an outer diameter of the generally cylindrical housing 136 is minimized in some embodiments.

FIG. 13C is a perspective view of a portion of the delivery device 130 and illustrates one embodiment of the retraction mechanism 141. As will be appreciated by those of ordinary skill in the art, the externally threaded sleeve 140 may be coupled to or formed integrally with a proximal end of the outer catheter shaft 134 such that movement of the externally threaded portion 140 causes corresponding movement of the outer catheter shaft 134. As illustrated in FIG. 13C, the externally threaded sleeve 140 includes a plurality of threads 142 that is structured to engage with one or more threads (not shown) on an inner bore of the knob 131. A pin 143 extending through at least a portion of the handle 132 is structured to mate with a longitudinal slot 145 formed in the externally threaded sleeve 140 to restrain the externally threaded sleeve 140 such that rotational movement of the knob 131 results in longitudinal movement of the externally threaded sleeve 140 and the outer catheter shaft 134 as will be appreciated by those of ordinary skill in the art. One or more additional pins and corresponding slots may also be used for additional stability and guidance. As illustrated in FIG. 13C, rotation of the knob 131 in the direction indicated by arrow 147A causes longitudinal movement of the externally threaded sleeve 140 in the direction indicated by arrow 149A, while rotation of the knob 131 in the direction indicated by arrow 147B causes longitudinal movement of the externally threaded sleeve 140 in the direction indicated by arrow 149B. Thus, movement of the externally threaded sleeve 140 in the direction indicated by arrow 149A "extends" the housing 136, while movement of the externally threaded sleeve 140 in the direction indicated by arrow 149B "retracts" the housing 136. As will be appreciated by those of ordinary skill in the art, the relationship between the direction of rotation of the knob 131 and the direction of longitudinal movement of the externally threaded sleeve 140 may be "reversed" by modifying the configuration of the threads. The retraction mechanism 141 can assume other forms configured to effectuate longitudinal extension and retraction of the outer catheter shaft 134/housing 136 relative to the inner catheter 135/end piece 137.

With reference again to FIGS. 13A and 13B, the end piece 137 of the inner catheter shaft 135 includes a central passage 144 that is structured to provide a pathway from the housing lumen 138 to an inner catheter shaft lumen 146 extending longitudinally along the length of the inner catheter shaft 137 into the handle 132. Thus, the central passage 144 in the end piece 137 is aligned with the inner catheter shaft lumen 146 to allow the control sutures 112 (FIG. 12A) to be received therein. More particularly, and as will be discussed in further detail to follow, the control sutures 112 are of a sufficient length to extend through the inner catheter shaft lumen 146 and into the handle 132 to maintain the radially compressed stented heart valve in the crimped configuration and allow deployment within the aortic annulus or other implantation position.

The handle 132 of the delivery device 130 includes a handle lumen 148 extending from a back side of the handle 132 into an interior thereof. The handle lumen 148, in combination with the inner catheter shaft lumen 146 of the inner catheter shaft 135 and the central passage 144 in the end piece 137, form a continuous pathway between the distal and proximal ends of the delivery device 130. The pathway allows for insertion of a stylet tool through the end piece 137 to grasp the control sutures 112 (FIG. 12A) and pull the control sutures 112 back through the delivery device 130 such that the control sutures 112 extends out of the handle lumen 148. The pathway may either be linear or nonlinear without departing from the intended scope of the present disclosure.

The various components of the delivery device 130, including the handle 132, the knob 131, the outer catheter shaft 134, the inner catheter shaft 135, and the housing 136, may be made of any material that is suitable for use in a surgical device, such as stainless steel or medical-grade plastics.

FIGS. 14A and 14B are side views of the delivery device 130 with a portion of the handle 132 removed to illustrate the operation of an engagement mechanism 133 in accordance with the present disclosure. Particularly, FIG. 14A illustrates the engagement mechanism 133 in an "engaged" position, while FIG. 14B illustrates the engagement mechanism 133 in a "disengaged" position. As illustrated in FIGS. 14A and 14B, the engagement mechanism 133 includes a trigger 150 that is pivotally coupled to a pivot pin 152 extending through the trigger 150 and connected to the handle 132. The engagement mechanism 133 further includes a first elongate gripper 154A coupled to the trigger 150 and a second elongate gripper 154B coupled to the handle 132 such that it is stationary. The first and second elongate grippers 154A and 154B are operable to grip the control sutures 112 (FIG. 12A) as will be hereinafter explained. The continuous pathway between the distal and proximal ends of the delivery device 130, which is shown in broken lines and labeled as element 151, passes between the first and second elongate grippers 154A and 154B.

As illustrated in FIGS. 14A and 14B, the engagement mechanism 133 further includes a torsion spring 156 operably coupling the trigger 150 to the housing 132. Those of ordinary skill in the art will appreciate that the engagement mechanism 133 may include a single torsion spring 156 or alternatively multiple torsion springs 156. In one embodiment, the engagement mechanism 133 may include a first torsion spring positioned adjacent a first side of the trigger 150 and a second torsion spring positioned adjacent a second side of the trigger 150.

The torsion spring 156 of FIGS. 14A and 14B includes a first leg 158 that is structured to engage the trigger 150 and a second leg 160 that is structured to engage the handle 132. As will be appreciated by those of ordinary skill in the art, the first and second legs 158 and 160 anchor the ends of the torsion spring 156 to the trigger 150 and the housing 132, respectively. The torsion spring 156 is structured to bias the trigger 150 in the engaged position illustrated in FIG. 14A.

In the engaged position of FIG. 14A, the first and second elongate grippers 154A and 154B are positioned in close proximity or in contact with one another to substantially block the path from the handle lumen 148 to the shaft lumen 146. In effect, the first and second elongate grippers 154A and 154B function as a clamping means for clamping and locking the control sutures 112 (FIG. 12A) within the handle 132 during the delivery procedure to maintain the stented heart valve 100 (FIG. 12A) in the crimped configuration.

In order to actuate the engagement mechanism 133 to the disengaged position of FIG. 14B, the surgeon simply pushes down on the trigger 150 against the force of the torsion spring 156. Pushing the trigger 150 against the force of the torsion spring 156 will cause the spring to become "loaded" or compressed. In the disengaged position, the first and second elongate grippers 154A and 154B are separated from one another and the control sutures 112 (FIG. 12A) are allowed to freely pass therebetween. When the control sutures 112 are properly positioned within the handle 132, the surgeon may allow the engagement mechanism 133 to move back to the engaged position of FIG. 14A by releasing the trigger 150.

Optionally, the engagement mechanism 133 includes a retention assembly 170 for retaining the trigger 150 in the disengaged position of FIG. 14B wherein the first and second elongate grippers 154A and 154B are separated from one another and the control sutures 112 (FIG. 12A) are allowed to freely pass therebetween. Although the retention assembly 170 is not a necessary component of the engagement mechanism 133, it increases the ease-of-use of the delivery device 130 because the surgeon is not required to keep the trigger 150 manually depressed with one hand while pulling the control sutures 112 through the delivery device 130 with the other hand.

Figure 15:
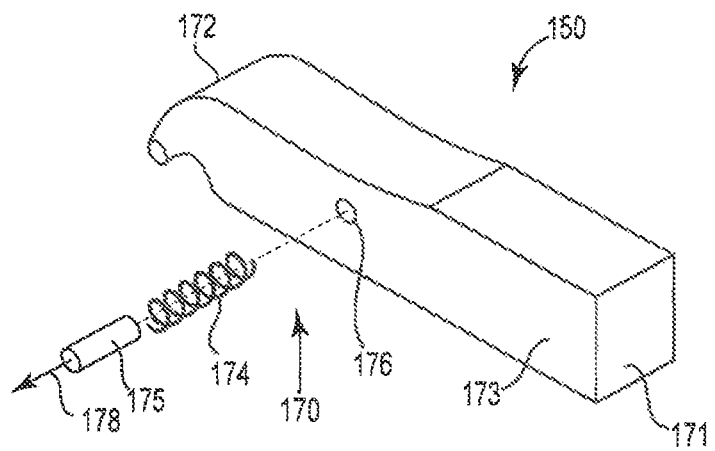
FIG. 15 is a perspective view of an engagement mechanism retention assembly in accordance with the present disclosure.

FIG. 15 is a perspective view of the trigger 150 illustrating the retention assembly 170 in accordance with the present disclosure. As illustrated in FIG. 15, the trigger 150 includes a distal end 171, a proximal end 172, and a side face 173. The retention assembly 170 includes a coil spring 174 and a retention pin 175 that are structured and sized to be received within a retention pin slot 176 within the side face 173 of the trigger 150. When assembled, the coil spring 174 is partially compressed between an inside end of the retention pin slot 176 and an adjacent end of the retention pin 175, thus biasing the retention pin in the direction indicated by arrow 178 away from the trigger 150.

Figure 16A:
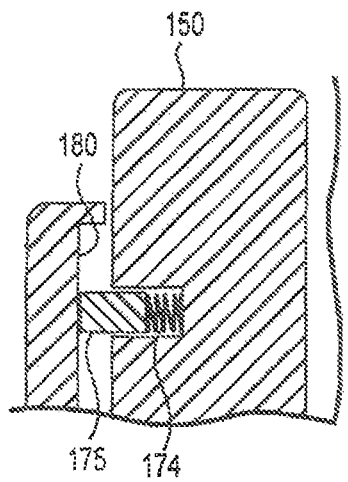
FIGS. 16A and 16B are diagrams illustrating the operation of the engagement mechanism retention assembly.
Figure 16B:
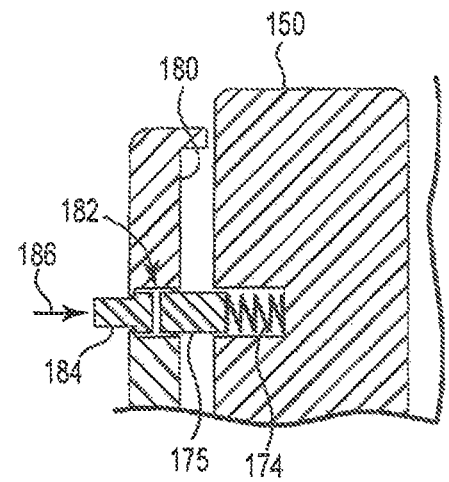

FIGS. 16A and 16B are diagrams illustrating the operation of the retention assembly 170. Particularly, FIG. 16A is a cross-sectional distal end view of the trigger 150 illustrating the trigger in the engaged position wherein the first and second elongate grippers 154A and 154B are in contact with one another as previously illustrated in FIG. 14A. In the engaged position, the retention pin 175 is biased toward and slidable against an internal surface 180 of the handle 132.

FIG. 16B is a cross-sectional distal end view of the trigger 150 illustrating the trigger 150 in the disengaged position wherein the first and second elongate grippers 154A and 154B are separated from one another to allow the control sutures 112 (FIG. 12A) to pass therebetween. As the trigger 150 is being actuated from the engaged position of FIG. 16A to the disengaged position of FIG. 16B, the retention pin 175 slides against the internal surface 180 of the handle 132 and "snaps" into a mating slot 182 in the handle 132 due to the outwardly directed spring force from the coil spring 174 to lock the trigger 150 in the disengaged position. As illustrated in FIG. 16B, when the retention pin 175 snaps into the mating slot 182, it pushes a push button 184 outwardly such that the push button 184 protrudes from the handle 132. With the trigger 150 locked in the disengaged position, the surgeon may insert a stylet tool through the handle lumen 148 and toward the end piece 137 to grasp and pull the control sutures 112 back through the handle of the delivery device 130. Once the control sutures 112 have been pulled through the handle 132 of the delivery device 130, the surgeon may once again move the engagement mechanism 133 to the engaged position by pressing the push button 184 in the direction indicated by arrow 186. Pressing the push button 184 in this direction releases the retention pin 175 from the mating slot 182 causing the trigger 150 to pivot back to the engaged position illustrated in FIG. 14A due to the force of the torsion spring 156 biasing the trigger 150 to the engaged position as previously discussed.

Those of ordinary skill in the art will appreciate that in alternative embodiments the position of the retention assembly 170 may be modified, such as by positioning the retention assembly on an opposing side of the trigger 150, without departing from the intended scope of the present disclosure. As will be further appreciated by those of ordinary skill in the art, numerous other engagement mechanisms and retention assemblies are possible and within the intended scope of the present disclosure. Thus, any suitable mechanical engagement means that is movable between an engaged position and a disengaged position to allow a suture to be pulled through the handle and locked therein may be used without departing from the intended scope of the present disclosure. Similarly, any suitable mechanical engagement means that may lock the retention assembly in the disengaged position may be used without departing from the intended scope of the present disclosure.

Figure 17:
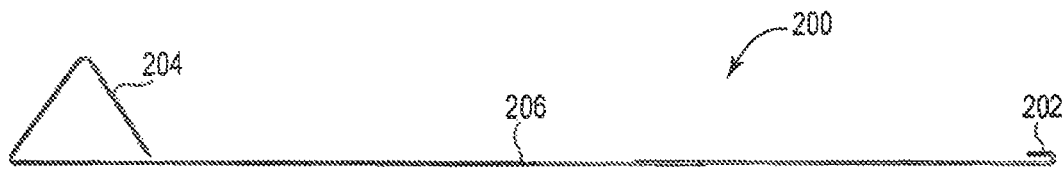
FIG. 17 is a side view of a stylet tool that may be used with the delivery device of the present disclosure.

FIG. 17 is a side view of a stylet tool 200 designed to be used in conjunction with the delivery device 130 (FIG. 13A) of the present disclosure. As illustrated in FIG. 17, the stylet tool 200 includes a flexible hook portion 202 at a distal end, a handle portion 204 at a proximal end, and an elongate main body 206 extending therebetween. As will be appreciated by those of ordinary skill in the art, the hook portion 202 is designed to grasp one or more control sutures 112 (FIG. 12A) when the stylet tool 200 is inserted through the delivery device 130 as will hereinafter be explained.

Now that embodiments of a crimping tool and a delivery device in accordance with the present disclosure have been set forth in detail, methods of using the crimping tool and delivery device to crimp a stented heart valve and deliver the heart valve to a patient will be described. More particularly, depending on the preference of the surgeon in operation, the stented heart valve 100 may be loaded into the housing 136 of the delivery device 130 in several different ways.

Figure 18:
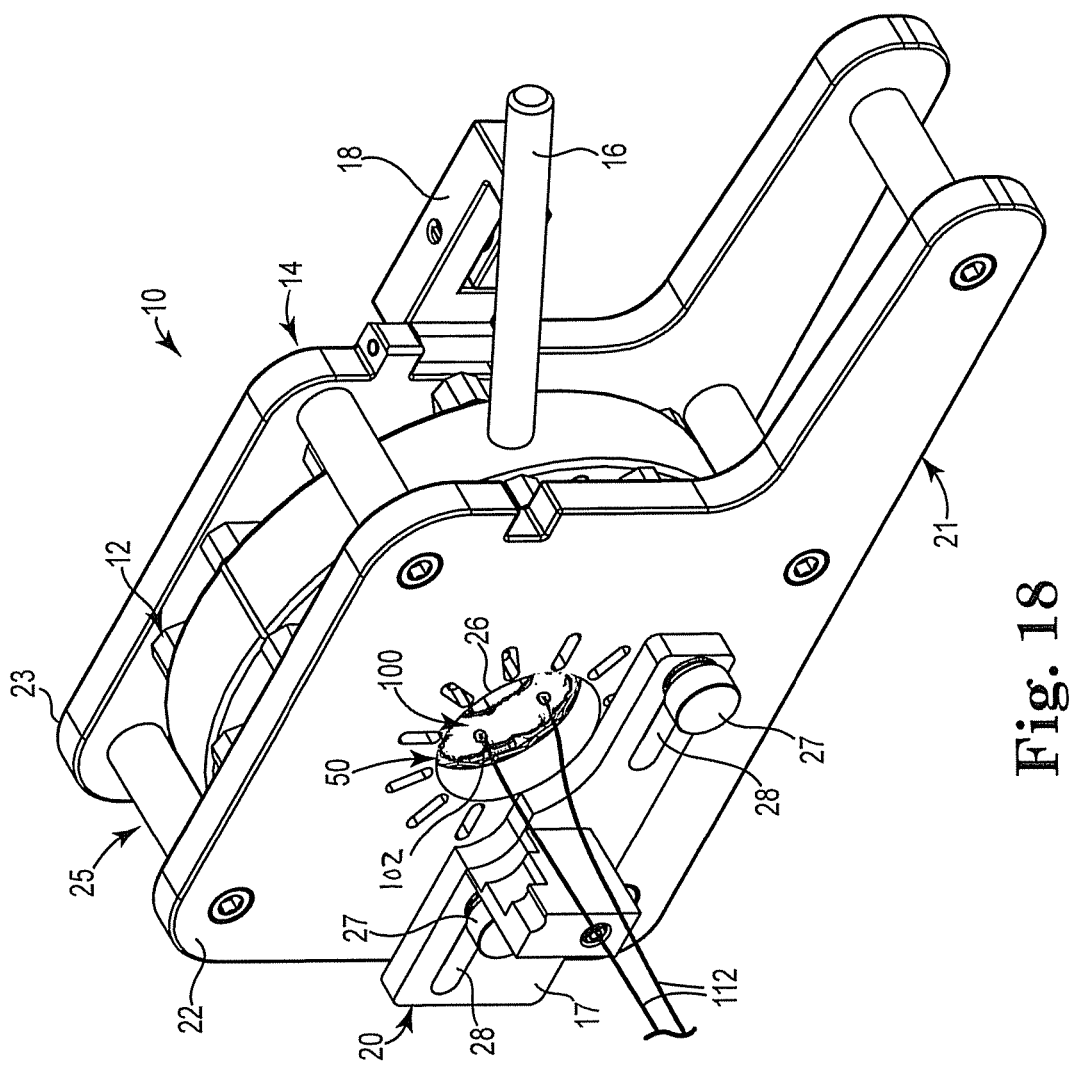
FIG. 18 is a perspective view of the crimping tool with the stented heart valve loaded therein.

In a first embodiment of loading a stented heart valve into a delivery device in accordance with the present disclosure and with reference to FIGS. 12A and 12B, the stented heart valve 100 is initially placed in chilled ice water so that the support stent 108 becomes malleable. As will be appreciated by those of ordinary skill in the art, any suitable cooling means may be used to chill the support stent 108 to make it malleable without departing from the intended scope of the present disclosure. Once the support stent 108 has been cooled and becomes malleable, the stented heart valve 100 is positioned within the chamber 50 of the crimping tool 10 with the compression assembly 12 in the uncrimped position as illustrated in FIG. 18. More particularly, the stented heart valve 100 is inserted into the chamber 50 such that the outflow end 104 is positioned adjacent to the back plate 23 and the inflow end 102 is positioned adjacent to the access aperture 26. As further illustrated in FIG. 18, the control sutures 112 are positioned such that they extend through the inflow end 102 of the stented heart valve 100 and outside of the crimping tool 10.

Figure 19:
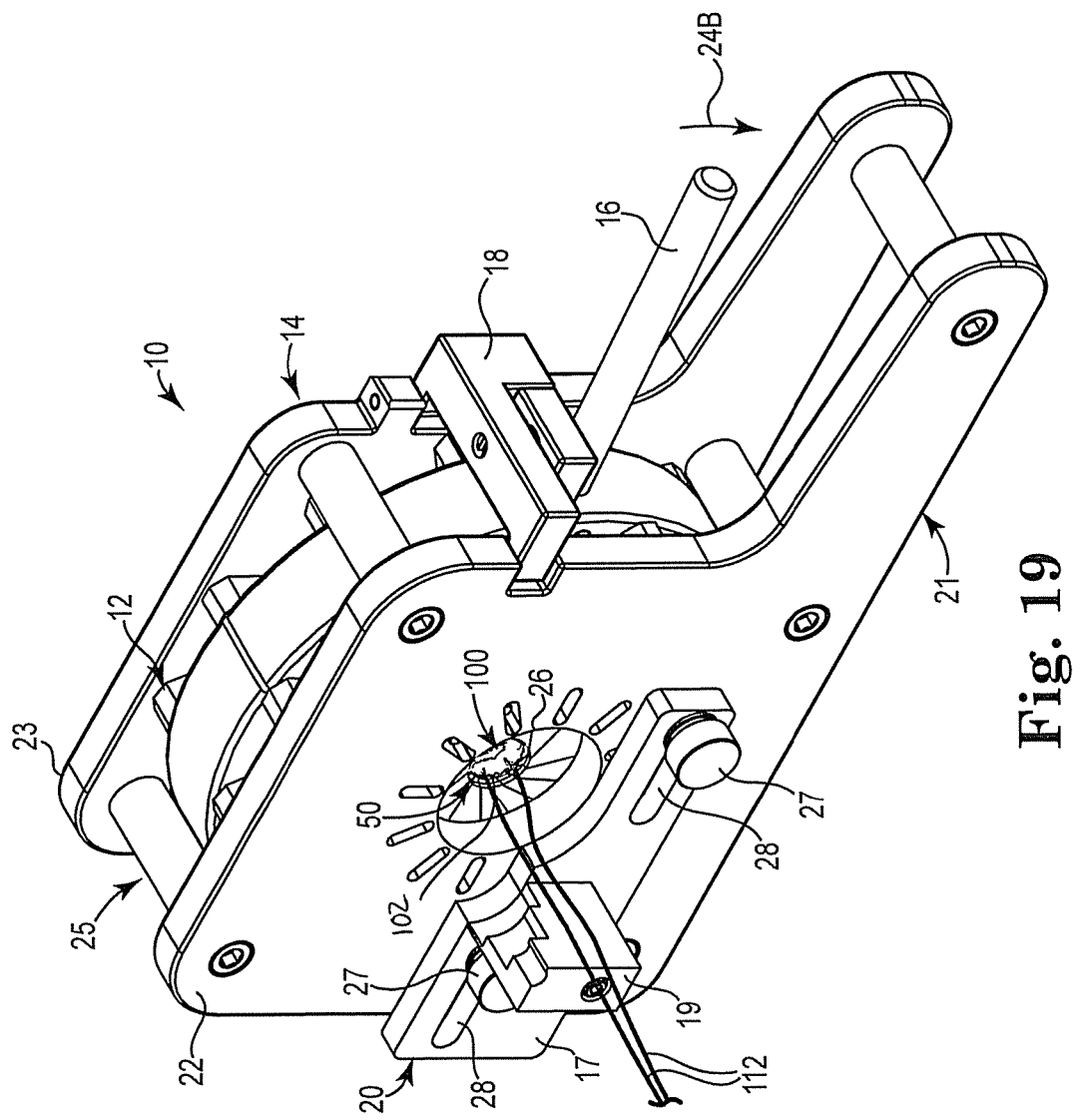
FIG. 19 is a perspective view of the crimping tool after the stented heart valve has been crimped.

Next, as illustrated in FIG. 19, the actuation lever 16 of the crimping tool 10 is moved in the clockwise direction 24B to radially crimp the stented heart valve 100 within the chamber 50. Once the stented heart valve 100 has been fully crimped, the lever lock 18 may be moved from the unlocked position of FIG. 18 to the locked position of FIG. 19. As previously discussed, moving the lever lock 18 to the locked position prevents the unintentional expansion of the compression assembly 12 and the stented heart valve 100 positioned therein from the crimped position back toward the uncrimped position.

Figure 20:
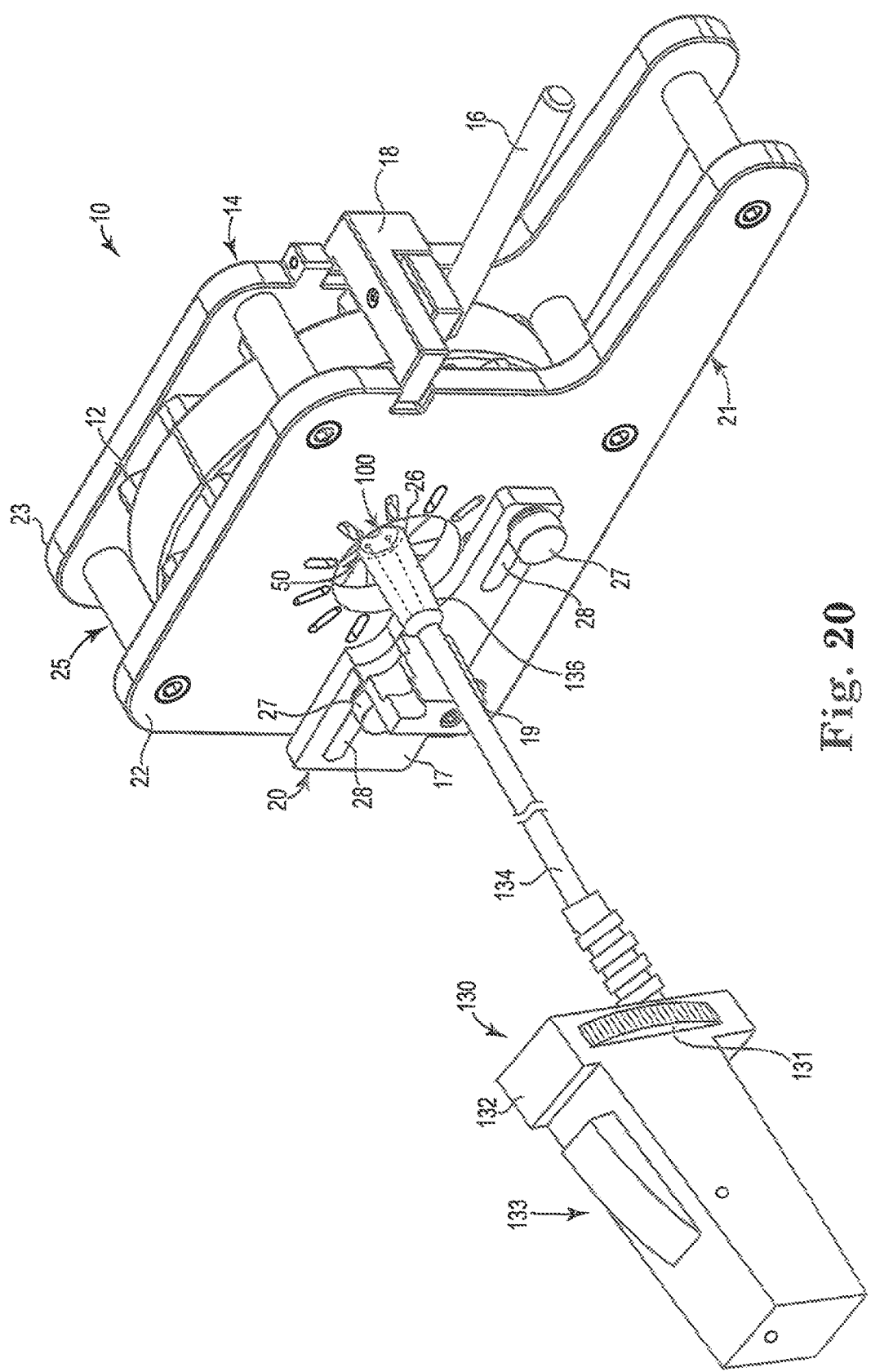
FIG. 20 is a perspective view of the delivery device aligned with the crimping tool.
Figure 21:
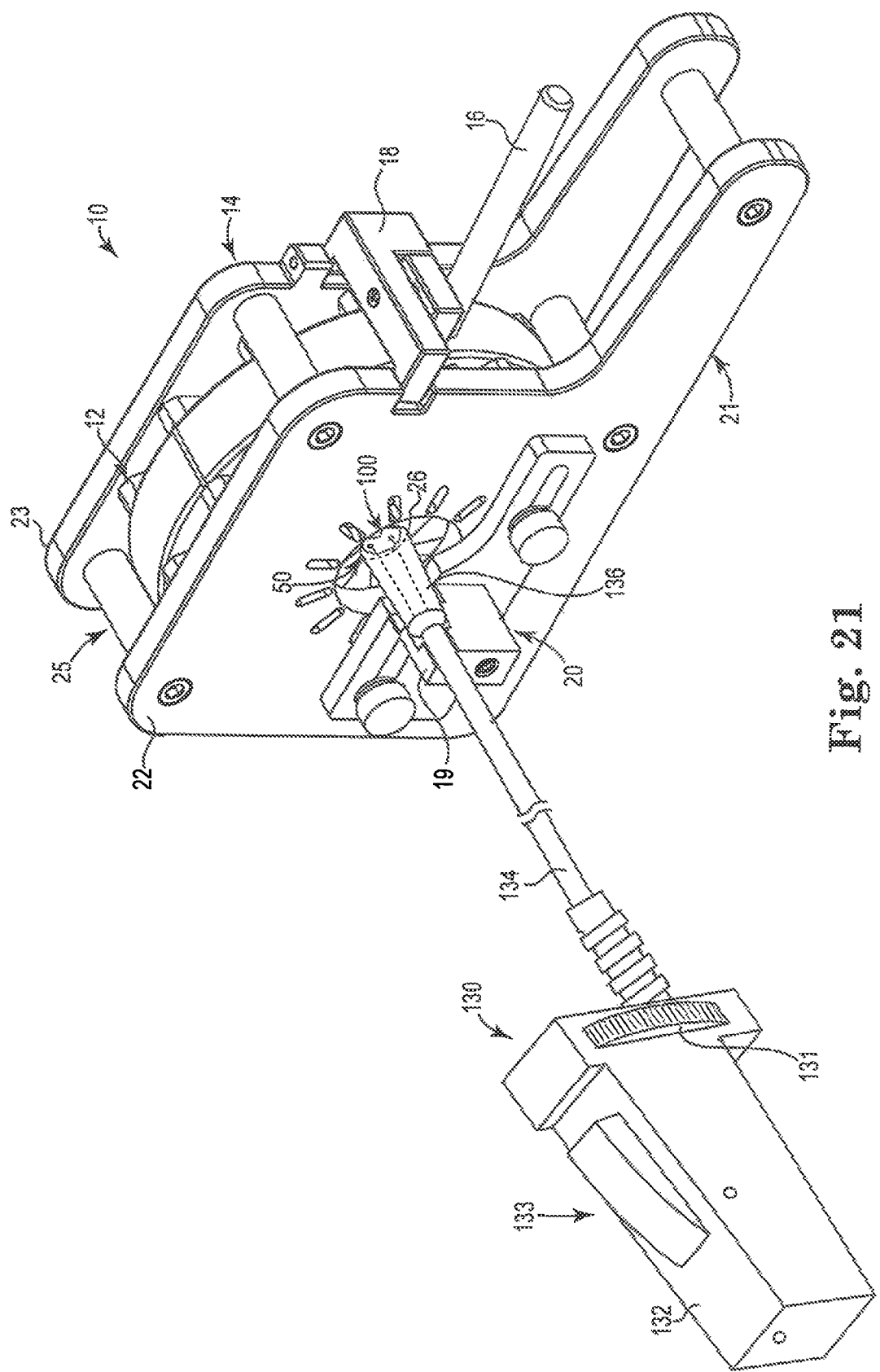
FIG. 21 is a perspective view of the delivery device positioned within the delivery device holder of the crimping tool.

Once the stented heart valve 100 has been crimped within the chamber 50, the housing 136 at the distal end of the outer catheter shaft 134 may be aligned with the chamber 50 such that the housing lumen 138 (FIG. 13A) is in communication with the interior of the chamber 50 as illustrated in FIG. 20. Then, the surgeon may slide the delivery device holder 20 horizontally such that the seat member 19 is aligned with the center axis of the access aperture 26 as previously discussed in detail with regard to FIG. 5. With the seat member 19 of the delivery device holder 20 aligned with the access aperture 26, the delivery device 130 may then be engaged with the seat member 19 as illustrated in FIG. 21.

Figure 22:
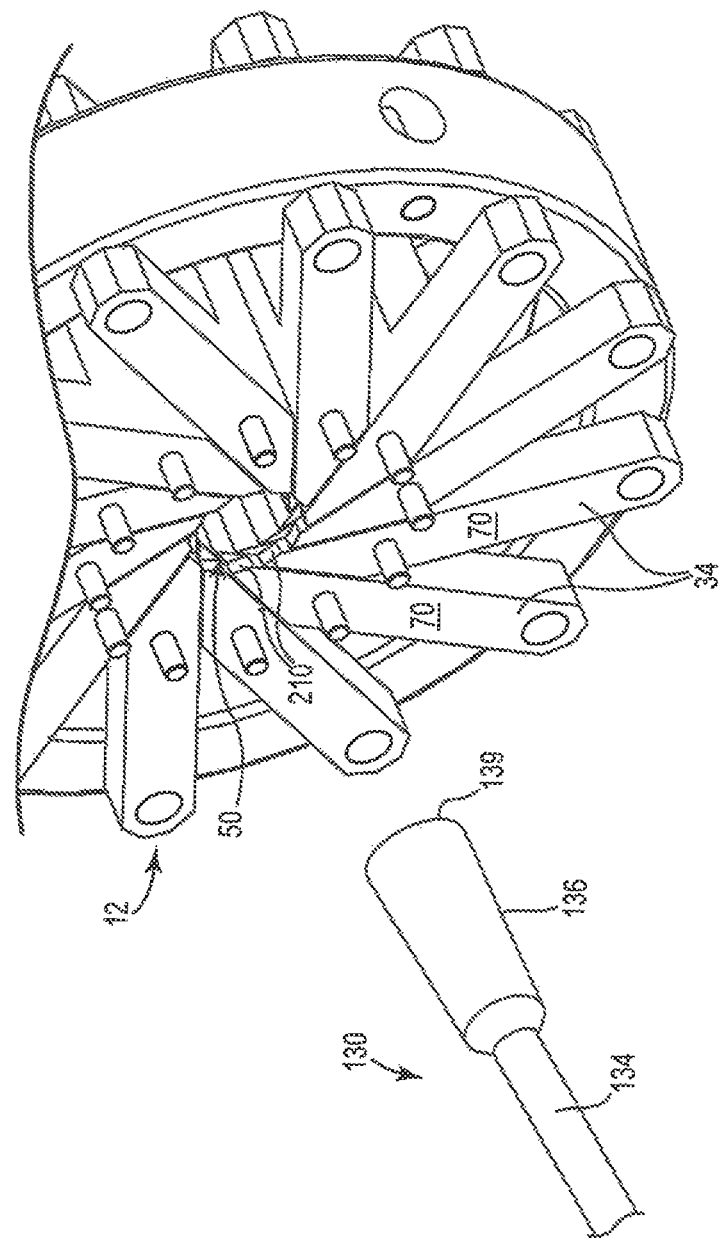
FIG. 22 is a perspective view of the compression assembly illustrating a plurality of recesses forming a stepped region for engagement with the delivery device.

To assist with the alignment of the housing 136 at the distal end of the outer catheter shaft 134 with the chamber 50, each of the bars 34 of the compression assembly 12 may include a recess 210 in the front face 70 as illustrated in FIG. 22. The plurality of recesses 210 together form a substantially circular stepped region that is structured to mate with and receive the distal edge 139 of the housing 136. In addition to assisting with the alignment of the housing 136 and the chamber 50, the stepped region formed by the plurality of recesses 210 also helps to maintain secure engagement between the delivery device 130 and the seat member 19 (FIG. 21) of the delivery device holder 20 (FIG. 21).

Figure 23:
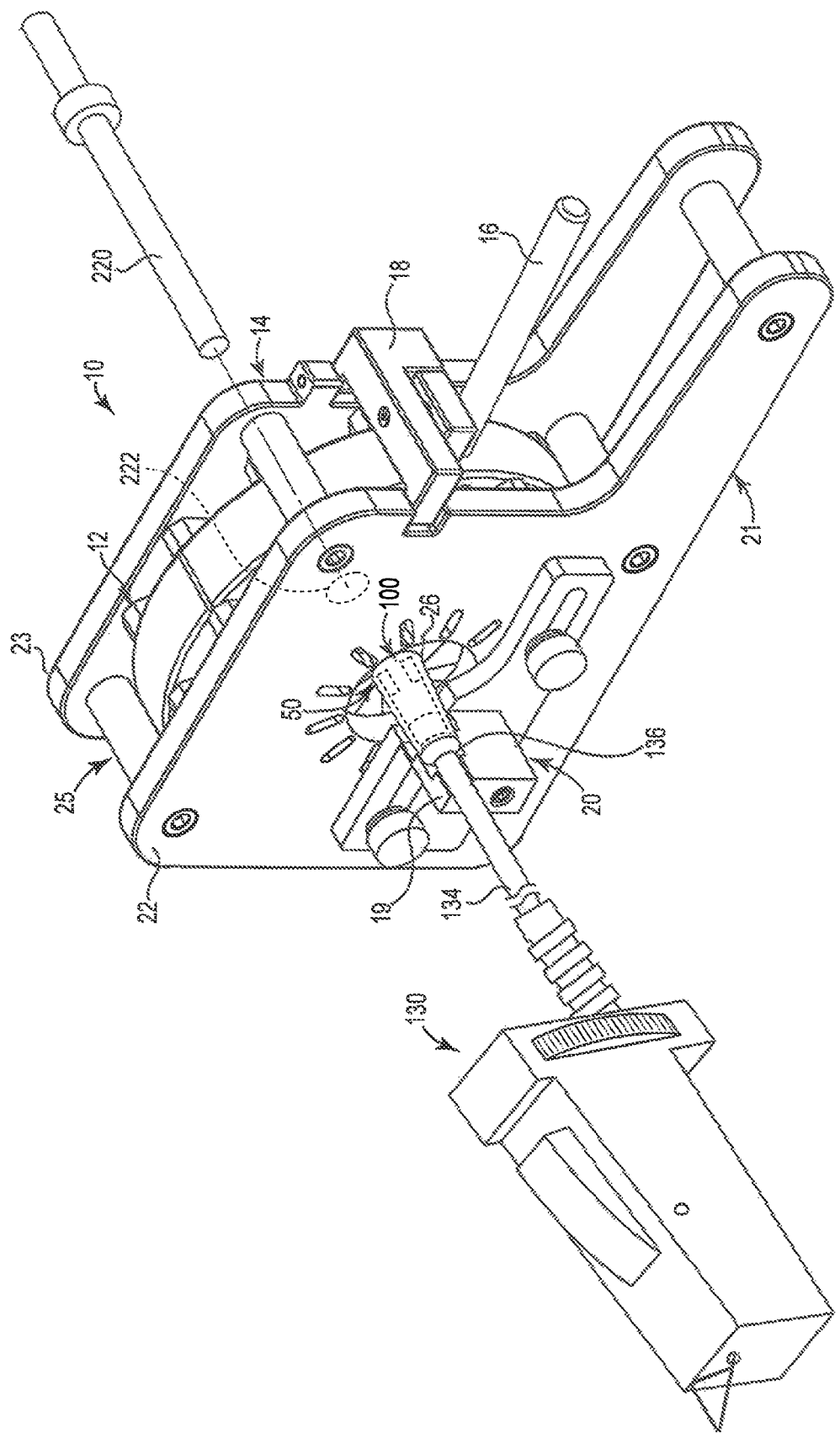
FIG. 23 is a perspective view of the crimping tool illustrating the crimped stented heart valve being loaded into the delivery device.

Next, an elongate cylindrical pusher tool 220 may be inserted through an aperture 222 in the back plate 23 of the crimping tool housing 14 as illustrated in FIG. 23 to manually push the crimped stented heart valve 100 into the housing 136 of the delivery device 130. Because the length L2 (FIG. 13B) of the housing 136 is substantially equivalent to the length L1 (FIG. 12B) of the stented heart valve 100 in some embodiments, the outflow end 104 (FIG. 12B) of the stented heart valve 100 is substantially aligned with the distal edge 139 of the housing 136 upon final insertion (with the inflow end (FIG. 12B) contacting, or nearly contacting, the end piece 137). As will be appreciated by those of ordinary skill in the art, care should be taken to ensure that the tail ends of the control sutures 112 (hidden in FIG. 23), which may be tied or otherwise attached together to form a continuous loop, are exposed at the inflow end 102 of the stented heart valve 100 and positioned next to the central passage 144 (FIG. 13A) of the end piece 137 (FIG. 13A). The flexible hook portion 202 (FIG. 17) of the stylet tool 200 is then inserted through the handle lumen 148 and positioned through the inner catheter shaft lumen 146 (FIG. 13A) and the central passage 144 (FIG. 13A) of the end piece 137. The control sutures 112 are then grasped by the flexible hook portion 202 within the housing 136. With the trigger 150 depressed such that the engagement mechanism 133 is in the disengaged position, the stylet tool 200 is pulled back through the inner catheter shaft lumen 146 and the handle lumen 148 to thread the control sutures 112 through the delivery device 130. The surgeon then manipulates the engagement mechanism 133 back to the engaged position to grasp and lock the control sutures 112 in place.

Figure 24:
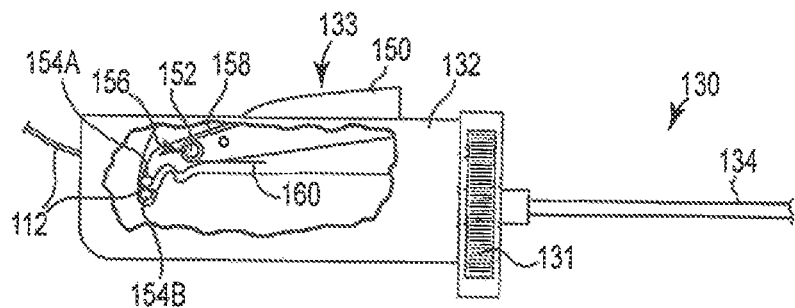
FIG. 24 is a diagram illustrating a control suture of the stented heart valve engaged by the engagement mechanism.

As best seen in FIG. 24, the engagement mechanism 133 locks and tensions the control sutures 112 in a taut position by engagement between the first and second elongate grippers 154A and 154B. As will be appreciated by those of ordinary skill in the art, tensioning of the control sutures 112 maintains the stented heart valve (not shown) in the radially crimped configuration throughout the deployment of the stented heart valve into the aortic annulus until the tension is released. As will further be appreciated by those of ordinary skill in the art, although the engagement mechanism 133 has been illustrated in the "fully" engaged and "fully" disengaged positions, the surgeon may manipulate the engagement mechanism 133 to a "partially" engaged position wherein the first and second elongate grippers 154A and 154B maintain at least some tension on the control sutures 112 but also allow the control sutures 112 to slide therebetween in a controlled manner. This allows the surgeon to re-expand the stented heart valve in a controlled manner during deployment within a patient as will be discussed in further detail to follow.

A second method of loading a stented heart valve into a delivery device in accordance with the present disclosure is generally similar to the first exemplary method described above with regard to FIGS. 18-24. However, instead of threading the control sutures 112 through the delivery device 130 after the stented heart valve 100 has been crimped and pushed into the housing 136 at the distal end of the outer catheter shaft 134, the control sutures 112 are threaded partially through the delivery device 130 and locked by the engagement mechanism 133 prior to pushing the stented heart valve into the housing 136. Once the crimped stented heart valve has been pushed into the housing 136, the excess length of the control sutures 112 may be pulled through the handle lumen 148 and once again grasped by the engagement mechanism 133 so that the control sutures 112 are taut. As will be appreciated by those of ordinary skill in the art, the initial threading of the control sutures 112 through the delivery device 130 may be performed either before of after the stented heart valve has been crimped.

Figure 25:
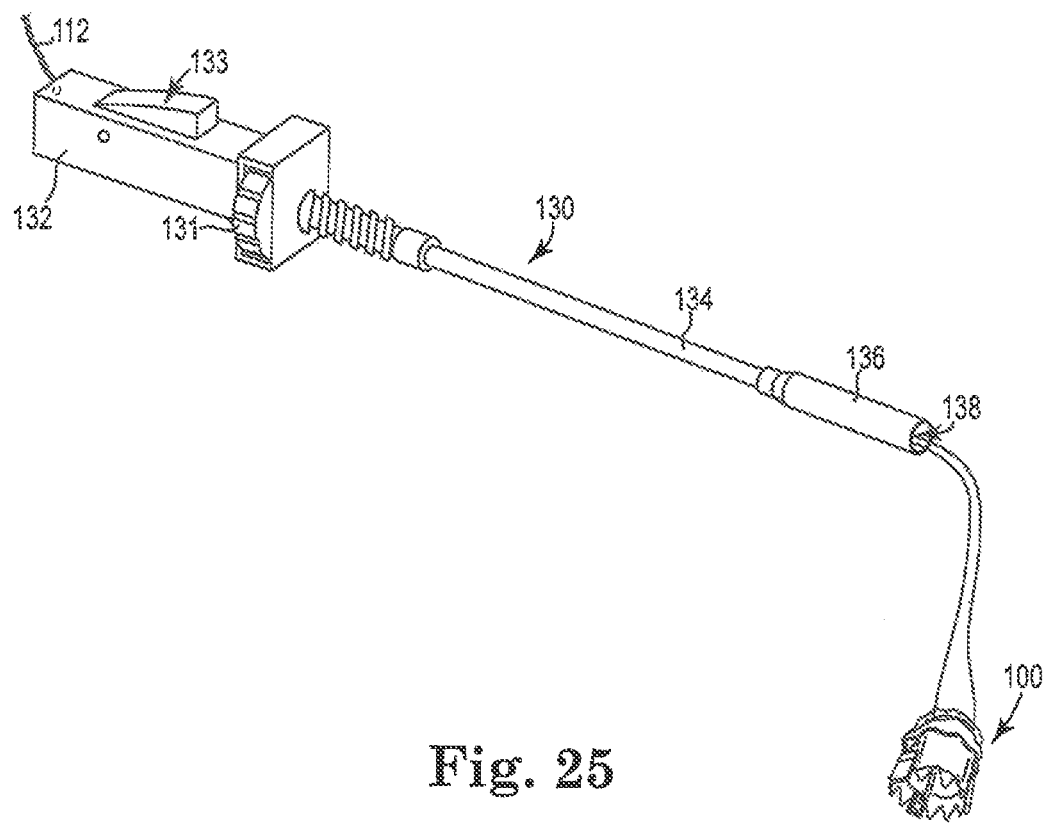
FIG. 25 is a perspective view of the delivery device with the stented heart valve hanging from a distal end thereof.

In a third embodiment of loading a stented heart valve into a delivery device 130, the flexible hook portion 202 of the stylet tool 200 is first inserted through the handle lumen 148 and positioned through the inner catheter shaft lumen 146 and the central passage 144 of the end piece 137. Control sutures 112 are then grasped by the flexible hook portion 202 near the housing 136 at the distal end of the outer catheter shaft 134. With the trigger 150 depressed such that the engagement mechanism 133 is in the disengaged position, the stylet tool 200 is pulled back through the inner catheter shaft lumen 146 and the handle lumen 148 to thread the control sutures 112 through the delivery device 130. The surgeon then manipulates the engagement mechanism 133 back to the engaged position to grasp and lock the control sutures 112 in an initial position in which the stented heart valve 100 hangs outside the housing 136 as best seen in FIG. 25. The stented heart valve 100 is then placed in chilled ice water so that the support stent 108 (FIG. 12B) becomes malleable. Once again, those of ordinary skill in the art will appreciate that any suitable cooling means may be used to chill the support stent 108 to make it malleable without departing from the intended scope of the present disclosure.

Once the support stent 108 has been cooled and becomes malleable, the stented heart valve 100 is positioned within the chamber 50 of the crimping tool 10, and the heart valve 100 is crimped by actuating the actuation lever 16 as previously described. The housing 136 at the distal end of the outer catheter shaft 134 may then be aligned with the chamber 50 such that the generally cylindrical shaft lumen 138 is in communication with the interior of the chamber, and the surgeon may slide the delivery device holder 20 horizontally such that the seat member 19 is aligned with the center of the access aperture 26 in the housing 14. With the seat member 19 of the delivery device holder 20 aligned with the access aperture, the delivery device 130 may then be positioned within the seat member 19. As will be appreciated by those of ordinary skill in the art, the delivery device holder 20 may alternatively be aligned with the access aperture and the delivery device 130 positioned therein prior to crimping the stented heart valve 100.

Next, the elongate cylindrical pusher tool 220 may be inserted through the aperture 222 in the back plate 23 of the crimping tool housing 14 as previously described to manually push the crimped stented heart valve 100 into the housing 136 of the delivery device 130 (within the delivery device 130 arranged in the extended position of the housing 136 as described above with respect to FIG. 13B). Once again, because the length L2 of the cone-shaped housing 136 is substantially equivalent to the length L1 of the stented heart valve 100 in some embodiments, the outflow end 104 of the stented heart valve 100 is substantially aligned with the distal edge 139 of the housing 136 upon final insertion (with the inflow end 102 contacting, or nearly contacting, the end piece 137). With the engagement mechanism 133 in the disengaged position, the surgeon then manually pulls the remaining length of the control sutures 112 through the inner catheter shaft lumen 146 and handle lumen 148. The engagement mechanism 133 is then actuated back to the engaged position to once again grasp and apply tension to the control sutures 112 to maintain the stented heart valve 100 in the radially crimped configuration during delivery of the valve.

As will be appreciated by those of ordinary skill in the art, the foregoing represent three stent crimping and loading methods in accordance with the present disclosure. However, numerous other methods are possible and within the intended scope of the present disclosure. Further, the number and order of steps described with regard to the three methods may be altered as will be appreciated by those of ordinary skill in the art.

The exemplary stent crimping and loading methods have been described with reference to the crimping tool 10 and the delivery device 130 merely for purposes of example and not limitation. Thus, the methods in accordance with the present disclosure may be performed using various other crimping tool and/or delivery device embodiments without departing from the intended scope of the present disclosure.

In one embodiment as discussed above, the delivery device of the present disclosure may be used for the transapical delivery of a crimped stented heart valve to an aortic annulus. In order to access the aortic annulus transapically, the surgeon first makes an incision in the chest at the approximate area of the apex of the heart. The surgeon may then use a trocar to pierce the apex of the heart. As will be appreciated by those of ordinary skill in the art, a separate trocar may be used to pierce the apex or alternatively a distal end of the delivery device may contain a sharpened edge that is capable of piercing the apex.

Figure 26A:
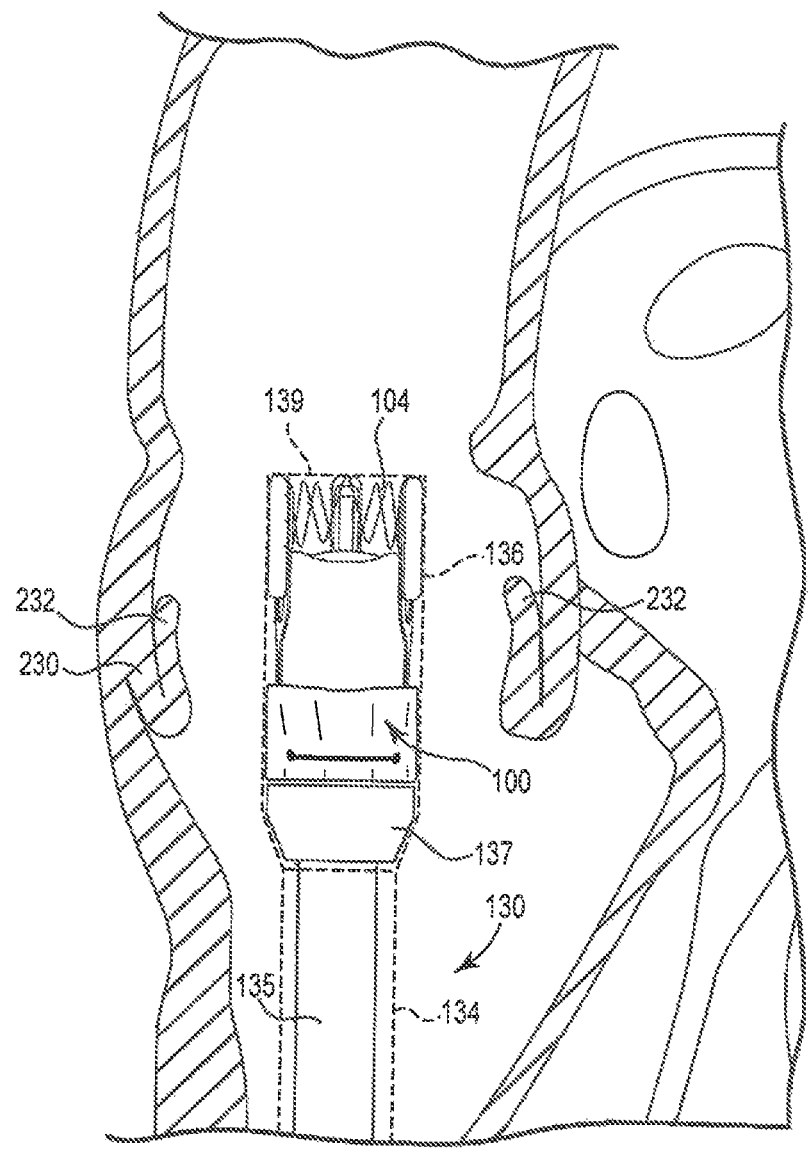
FIGS. 26A-26C are diagrams illustrating a transapical method of delivering a stented heart valve to an aortic annulus in accordance with the present disclosure.

Once the apex of the heart has been pierced, the surgeon positions the delivery device 130 within the aortic annulus 230 as illustrated in the partial cross-sectional view of FIG. 26A pushing aside the native leaflets 232 such that the distal edge 139 of the housing 136, and thus the outflow end 104 of the stented heart valve 100, is aligned with the outflow region of the native valve. The housing 136 and the outer catheter shaft 134 are illustrated in broken lines to allow visualization of the stented heart valve 100, the inner catheter shaft 135, and the end piece 137. In a typical transapical procedure, the surgeon visualizes correct anatomical placement of the delivery device 130 within the aortic annulus 230 of the native valve via fluoroscope or other visualization means known in the art.

Figure 26B:
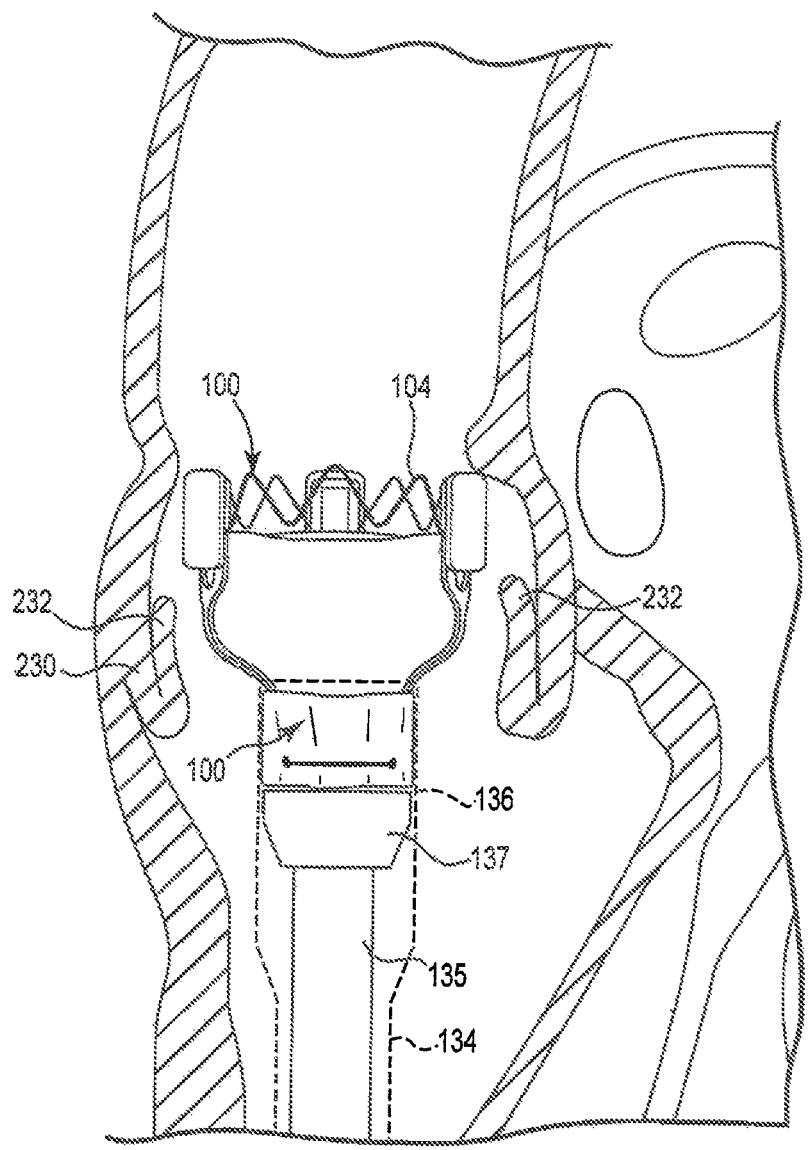

As illustrated in FIG. 26B, the surgeon then actuates the retraction mechanism 141 (FIG. 13C) to begin to retract the outer catheter shaft 134 relative to the inner catheter shaft 135 to expose the outflow end 104 of the stented heart valve 100. Interface between the end piece 137 and the stented heart valve 100 assists in maintaining a spatial position of the stented heart valve 100 during retraction of the outer catheter shaft 134/housing 136. In this regard, by forming the end piece 137 as a "bumper" element, contact with the end piece 137 does not damage the stented heart valve 100. The surgeon may then slowly release the tension placed on the control sutures 112 by the controlled manipulation of the engagement mechanism 133 (FIG. 14A). As will be appreciated by those of ordinary skill in the art, warm bodily fluids cause the exposed portion of the stented heart valve 100, i.e. the outflow end 104, to start to expand to the "remembered" shape as further illustrated in FIG. 26B. Alternatively or in addition, the surgeon may apply a warm solution to the implantation site to promote re-expansion of the stented heart valve 100, such as a warm saline solution.

As the surgeon continues to actuate the retraction mechanism 141 (FIG. 13C) to retract the outer catheter shaft 134 relative to the inner catheter shaft 135 and manipulate the engagement mechanism 133 (FIG. 14A) to release the tension placed on control sutures 112, additional portions of the stented heart valve 100 may be expanded within the aortic annulus.

As will be appreciated by those of ordinary skill in the art, transapical delivery and subsequent implantation of the heart valve in accordance with the disclosure is done on a beating heart. In particular, the method of implanting a heart valve in a beating heart prevents backflow of blood from the aorta. During normal ventricular systole, pressure rises in the left ventricle. When the pressure in the left ventricle rises above the pressure in the aorta, the aortic valve opens, allowing blood to exit the left ventricle into the aorta. When ventricular systole ends, pressure in the left ventricle rapidly drops. When left ventricular pressure decreases, pressure in the aorta forces the aortic valve to close. However, diseased native leaflets do not close or do not close fully which causes arterial backflow into the left ventricle. Similarly, when stented heart valves are deployed, the stent portion urges the diseased native leaflets against the arterial wall and they cannot close or close only partially resulting in back flow into the left ventricle. As the stented heart valve in accordance with an aspect of the disclosure is being deployed, back flow from the aorta causes the prosthetic leaflets 115 (FIG. 12A) to radially expand against the stented portion preventing backflow, which allows a surgeon to do replacement heart valve surgery on a beating heart.

Figure 26C:
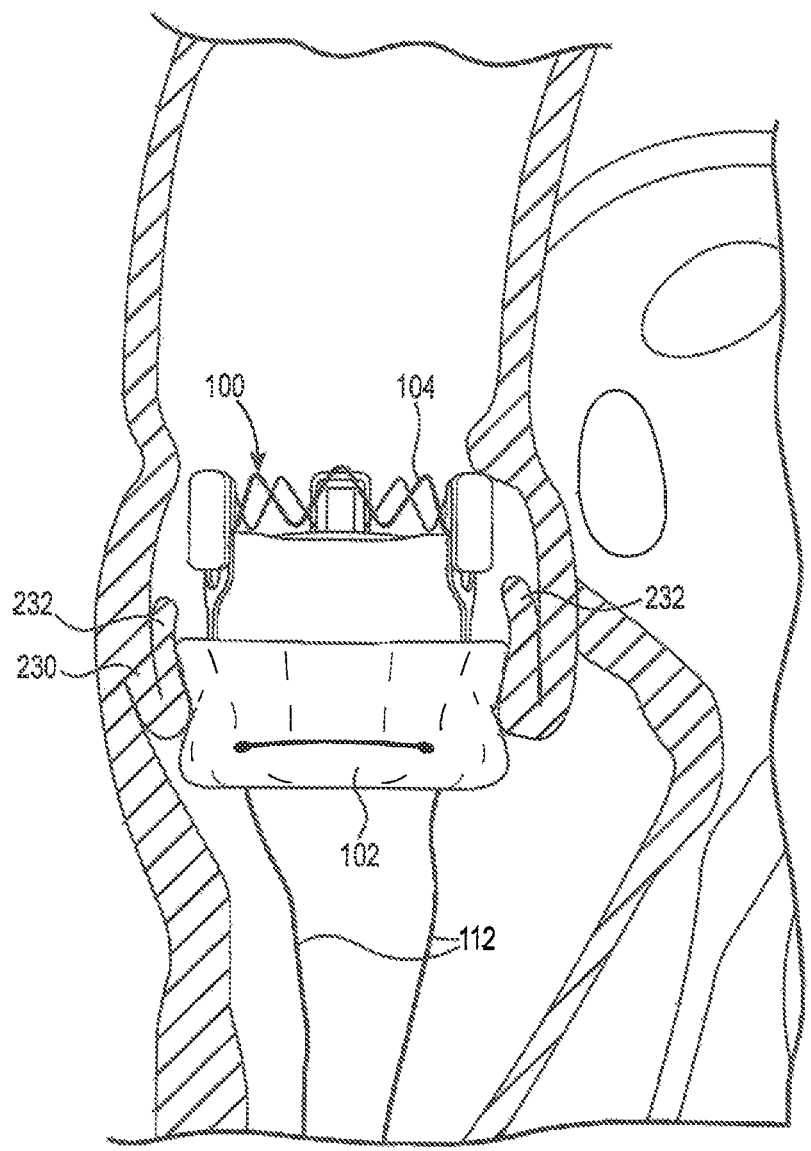

Once the stented heart valve 100 is fully exposed and the tension on control sutures 112 is released, the inflow end 102 of the stented heart valve 100 completely expands in the aortic annulus 230 where it friction fits and seals into place. The delivery device 130 is then slowly removed from the aortic annulus 230. FIG. 26C illustrates the stented heart valve 100 in its fully expanded configuration with the inflow end 102 engaging the aortic annulus 230. As will be appreciated by those of ordinary skill in the art, after the stented heart valve 100 is fully expanded within the aortic annulus 230, the control sutures 112 may be manually removed from the stented heart valve 100 in any suitable manner as they are no longer needed.

Although the heart valve delivery device has been described with reference to the delivery of a stented trileaflet replacement valve within the aortic annulus, those of ordinary skill in the art will appreciate that heart valve delivery devices in accordance with the present disclosure may be used for the delivery of many types of valves and in various implantation locations. Thus, the transapical delivery of a stented heart valve within the aortic annulus has been described merely for purposes of example and not limitation.

What is claimed is:

1. A delivery device for a stented heart valve comprising:
a handle;
an inner catheter shaft extending from the handle and having an enlarged bumper element at a distal terminal end of the inner catheter shaft, wherein a distal-most face of the bumper element defines a central passage and a complete, uninterrupted annular surface defined as an area between the central passage and a maximum outer diameter of the distal-most face of the bumper element, wherein the maximum outer diameter is a complete uninterrupted circle and further wherein the distal-most face is configured to abut the stented heart valve;
an outer catheter shaft extending from the handle and slidably coupled around the inner catheter shaft, the outer catheter shaft including a generally cylindrical housing at a distal side that is structured to receive the bumper element therein; and
a retraction mechanism for controlling longitudinal movement of the outer catheter shaft relative to the inner catheter shaft; wherein the retraction mechanism can move the outer catheter shaft into an extended position and a retracted positon;
wherein, when the outer catheter shaft is in the retracted position, no part of the delivery device is more distal than the distal-most face.

2. The delivery device of claim 1, wherein the housing defines a housing lumen sized to slidably receive the bumper element.

3. The delivery device of claim 2, wherein an outer diameter of the bumper element is less than a diameter of the housing lumen and greater than a diameter of a lumen defined by the outer catheter shaft proximal the housing.

4. The delivery device of claim 2, wherein the housing lumen is configured to receive a crimped stented heart valve.

5. The delivery device of claim 1, wherein the retraction mechanism includes a control knob rotatably maintained by the handle and connected to the outer catheter shaft, and further wherein the retraction mechanism is configured such that rotation of the control knob causes the outer catheter shaft to move longitudinally relative to the inner catheter shaft.

6. The delivery device of claim 5, wherein the retraction mechanism further includes a threaded sleeve mounted to the outer catheter shaft and threadably connected to the control knob.

7. A system for replacing a native heart valve, the system comprising:
a stented heart valve including a stent maintaining a valve structure; and
a delivery device including:
a handle,
an inner catheter shaft extending from the handle and having an enlarged bumper element at a distal terminal end of the inner catheter shaft, wherein the bumper element is configured to interface with the stented heart valve, wherein a distal-most face of the bumper element defines a central passage and a complete, uninterrupted annular surface defined as an area between the central passage and a maximum outer diameter of the distal-most face of the bumper element and further wherein the maximum outer diameter is a complete uninterrupted circle,
an outer catheter shaft extending from the handle and slidably coupled around the inner catheter shaft, the outer catheter shaft including a generally cylindrical housing at a distal side that is structured to receive the bumper element therein,
a retraction mechanism for controlling longitudinal movement of the outer catheter shaft relative to the inner catheter shaft in an extended position and a retracted position; wherein, when the outer catheter shaft is in the retracted position, no part of the delivery device is more distal than the distal-most face;
wherein the system provides a loaded state in which the stented heart valve is held in a crimped arrangement within the housing and an entirety of the stented heart valve is distal the bumper element.

8. The system of claim 7, wherein a distal end of the housing being distal the bumper element in the extended position, and further wherein the loaded state includes the outer catheter shaft in the extended position.

9. The system of claim 8, wherein the loaded state includes a first end of the stented heart valve abutting the distal-most face of the bumper element.

10. The system of claim 9, wherein the loaded state further includes a second, opposite end of the stented heart valve located adjacent the distal end of the housing.

11. The system of claim 8, wherein in the extended position a housing lumen is defined by the housing, the housing lumen having a longitudinal length from the bumper element to the distal end of the housing, and further wherein the longitudinal length of the housing lumen is substantially equivalent to a longitudinal length of a stented heart valve.

12. The system of claim 7, wherein the housing defines a housing lumen sized to slidably receive the bumper element.

13. The system of claim 12, wherein an outer diameter of the bumper element is less than a diameter of the housing lumen and greater than a diameter of a lumen defined by the outer catheter shaft proximal the housing.

14. The system of claim 7, wherein the retraction mechanism includes a control knob rotatably maintained by the handle and connected to the outer catheter shaft, and further wherein the retraction mechanism is configured such that rotation of the control knob causes the outer catheter shaft to move longitudinally relative to the inner catheter shaft.

15. The system of claim 14, wherein the retraction mechanism further includes a threaded sleeve mounted to the outer catheter shaft and threadably connected to the control knob.

16. The system of claim 7, wherein the system further includes a suture, and further wherein the loaded state includes the suture extending from the stented heart valve, through the inner catheter shaft, and through the handle.

* * * * *